United States Patent
Felzmann et al.

(10) Patent No.: US 9,303,246 B2
(45) Date of Patent: Apr. 5, 2016

(54) METHODS FOR PRODUCING DENDRITIC CELLS WITH AN SIRNA THAT INTERFERES WITH MAPKAPK2 EXPRESSION

(75) Inventors: Thomas Felzmann, Riederberg (AT); Alexander Michael Dohnal, Vienna (AT)

(73) Assignee: TRIMED BIOTECH GMBH, Vienna (AT)

( * ) Notice: Subject to any disclaimer, the term of this patent is extended or adjusted under 35 U.S.C. 154(b) by 718 days.

(21) Appl. No.: 12/747,759

(22) PCT Filed: Dec. 12, 2008

(86) PCT No.: PCT/EP2008/010606
§ 371 (c)(1),
(2), (4) Date: Jul. 28, 2010

(87) PCT Pub. No.: WO2009/074341
PCT Pub. Date: Jun. 18, 2009

(65) Prior Publication Data
US 2010/0285072 A1    Nov. 11, 2010

(30) Foreign Application Priority Data

Dec. 12, 2007  (EP) .................................... 07450233

(51) Int. Cl.
*C12N 15/113* (2010.01)
*C12N 5/0784* (2010.01)
*A61K 39/00* (2006.01)

(52) U.S. Cl.
CPC .............. *C12N 5/0639* (2013.01); *C12N 5/064* (2013.01); *A61K 2039/5154* (2013.01); *C12N 2501/052* (2013.01); *C12N 2501/22* (2013.01); *C12N 2501/23* (2013.01); *C12N 2501/24* (2013.01); *C12N 2501/70* (2013.01); *C12N 2510/00* (2013.01)

(58) Field of Classification Search
None
See application file for complete search history.

(56) References Cited

U.S. PATENT DOCUMENTS

| 7,867,488 B2 * | 1/2011 | Felzmann | 424/93.7 |
| 2009/0010927 A1 * | 1/2009 | Yaffe et al. | 424/133.1 |
| 2010/0285072 A1 * | 11/2010 | Felzmann et al. | 424/278.1 |

FOREIGN PATENT DOCUMENTS

WO    WO 2007/117682    10/2007

OTHER PUBLICATIONS

Zaru et al., Nature Immunology Advance Online Publication, published online Sep. 30, 2007; doi:10.1038/ni1517.*
Adler et al., Blood 109 (10): 4351-4359, 2007.*
Huber et al., PLoS One 3 (10): 1-7, published Oct. 1, 2008.*
Kalady et al., "Sequential delivery of maturation stimuli increases human dendritic cell IL-12 production and enhances tumor antigen-specific immunogenicity," *J. Surg. Res.*, 116:24-31, 2004.
Koya et al., "Potent maturation of monocyte-derived dendritic cells after CD40L lentiviral gene delivery," *J. Immunoth.*, 26:451-460, 2003.
Liu et al., "Adenovirus-mediated CD40 ligand gene-engineered dendritic cells elicit enhanced CD8(+) cytotoxic T-cell activation and antitumor immunity," *Cancer Gene Therapy*, 9:202-208, 2002.
Office Communication issued in European Patent Application No. 08859543.4, dated Aug. 8, 2013.
Dohnal et al., "Phase 1 study of tumor Ag-loaded IL-12 secreting semi-mature DC for the treatment of pediatric cancer", *Cytotherapy*, 9(8):755-770, 2007.
Kalady et al., "Sequential Delivery of Maturation Stimuli Increases Human Dendritic Cell IL-12 Production and Enhances Tumor Antigen-Specific Immunogenicity", *Journal of Surgical Research*, 116:24-31, 2004.
Koya et al., "Potent Maturation of Monocyte-Derived Dendritic Cells After CD40L Lentiviral Gene Delivery", *Journal of Immunotherapy*, 26(5):451-460, 2003.
Liu et al., "Adenovirus-mediated CD40 ligand gene-engineered dendritic cells elicit enhanced CD8+ cytotoxic T-cell activation and antitumor immunity", *Cancer Gene Therapy*, 9:202-208, 2002.
Zu, Y et al.: "The primary structure of a human MAP kinase activated protein kinase 2", Biochem Biophys Res Commun., vol. 200 (1994), pp. 1118-1124.
*Homo sapiens* mitogen-activated protein kinase-activated protein kinase 2 (MAPKAPK2), mRNA (http://www.ncbi.nlm.nih.gov/nuccore/NM_004759.1).
Liu, Gentao et al.: "Small interference RNA modulation of IL-10 in human monocyte-derived dendritic cells enhances the Th1 response", Eur. J. Immunol., vol. 34, (2004), pp. 1680-1687.
Igietseme, Joseph U. et al.: Suppression of Endogenous IL-10 Gene Expression in Dendritic Cells Enhances Antigen Presentation for Specific Th1 Induction: Potential for Cellualr Vaccine Development:, The Journal of Immunology, (2000), pp. 4212-4219.

* cited by examiner

*Primary Examiner* — Phillip Gambel
(74) *Attorney, Agent, or Firm* — Norton Rose Fulbright US LLP

(57) ABSTRACT

The present invention relates to a method for producing dendritic cells and their use in medicaments by genetic engineering aimed at functionally improving their therapeutic efficacy in the treatment of cancer, microbial infections, allergies, auto-immune diseases or organ and stem cell transplant rejection.

6 Claims, 9 Drawing Sheets

METHODS FOR PRODUCING DENDRITIC CELLS WITH AN SIRNA THAT INTERFERES WITH MAPKAPK2 EXPRESSION

This application is a national phase application under 35 U.S.C. §371 of International Application No. PCT/EP2008/010606 filed 12 Dec. 2008, which claims priority to European Application No. 07450233.7 filed 12 Dec. 2007. The entire text of each of the above-referenced disclosures is specifically incorporated herein by reference without disclaimer.

The present invention relates to a method for producing and genetically engineering dendritic cells (DC) and uses thereof.

During the last years the dendritic cell (DC) has been recognised as the central regulator of immunity. Human DCs are generated by in vitro differentiation from haematopoietic stem cells or peripheral blood monocytes in the presence of growth factors, typically interleukin (IL) 4 and granulocyte-macrophage colony-stimulating factor (GM-CSF). Recent evidence suggests that DCs have the capacity to flexibly respond to the encounter of microbial, traumatic, or metabolic stress. Thus, DCs do not only differentiate into one subtype that fulfils a particular function, e.g. activation or tolerance, type 1 or type 2 T-helper lymphocyte (Th1, Th2) polarisation, but assume distinct functional states in a time-kinetic fashion appropriate to the challenges encountered in a given environment (FIG. 1).

Monocytes leave the blood stream to enter various tissues and to become what is conventionally referred to as immature DCs (iDC). These iDCs are sentinels that sample their environment by taking up material from the extra cellular fluid as well as apoptotic bodies from physiologically dying cells, process, and present this material without co-stimulation in a tolerance-inducing form to T-lymphocytes. The tolerance-inducing iDC phenotype may be considered the default status of DCs. This state is maintained until the iDC encounters a danger signal that may be a pathogen associated molecular pattern (PAMP) transmitted by toll-like receptors (TLR), inflammatory cytokines, or T-lymphocyte derived signalling, most prominently mediated by CD40/CD40L interaction. This process is referred to as DC maturation, which coincides with a sequence of functional changes. These functional changes take place over a period of approximately 2 days, after which the DCs reach a status that is referred to as mature DCs (mDCs). Most prominently, the DC starts to up-regulate co-stimulatory molecules such as the B7 family members CD80 and CD86. This enables the DC to deliver an activating rather than a suppressive signal to T-lymphocytes that carry a T-cell receptor capable of interacting with an antigenic peptide in a complex with major histocompatibility complex (MHC) molecules on the DC membrane. At this stage also a stimulus-dependent polarisation takes place, with DCs secreting IL-12 as well as IL-12 family cytokines favouring a type 1 immune response that subsequently supports cellular immunity mediated by cytotoxic T-lymphocytes (CTL). IL-12 secretion is generally triggered by engagement of TLRs with their ligands, for example TLR4 engagement with LPS, but also by interaction of soluble or cell membrane bound CD40L molecules with CD40 on DCs. In contrast, the absence of IL-12 release triggers a type 2 polarisation that initiates a humoral immune response by supporting B-lymphocytes. Initiation of DC maturation without IL-12 secretion is accomplished by exposure of iDCs with cytokine cocktails that typically contain TNF-α and PG-E2 as well as various inflammatory cytokines including but not limited to type I and type II interferons, IL-1, or IL-6.

IL-12 release ceases after about 24 hours indicating that the encounter between DCs and T-lymphocytes needs to take place within that time window to allow efficient type 1 polarisation and CTL activation. In contrast, the expression of co-stimulatory molecules reaches its maximum after 2 days. Since per definition a mature DC is characterised only phenotypically by maximum expression of co-stimulatory molecules but not functionally, the IL-12 releasing type 1 polarising DC is referred to as semi-mature (sm) DC. After approximately 2 days the DC reaches the stage of so called maturity. During the second day of its differentiation the DCs loose their immune stimulatory capacity and acquire immune suppressive properties by up-regulation of molecules that mediate negative regulatory feedback loops (FIG. 1). The biological significance of this differentiation phase is the necessity of keeping immune responses under strict control. An activated immune cell, particularly a CTL that is enabled for the killing of other cells, poses a considerable threat to an organism. This is exemplified by the pathological consequences of immune responses that dodged their control: autoimmune disease such as type I diabetes or multiple sclerosis. Therefore, the same DC that during day 1 after encountering a maturation signal primes immune responses will dampen this same immune response during day 2 of their differentiation process. Therefore, mature DCs are in fact not as originally thought immune stimulatory but rather immune suppressive cells and therefore inadequate for therapeutic interventions aimed at immune stimulation such as their use in cancer immune therapy or the treatment of microbial diseases.

It is important to distinguish between immature (tolerance maintaining), semi-mature DCs (immune stimulatory), and mature (immune suppressive) DCs (FIG. 1). An iDC as outlined above maintains tolerance against autoantigens. An smDC has encountered one of the maturation stimuli described above and has irreversibly committed to differentiation into mDCs within approximately 2 days. Importantly, only during the first one of those 2 days it is enabled for IL-12 release, initiation of type I immune polarisation, and consequently support of a CTL mediated immune response. Once a maturing DC enters the second phase of differentiation after one day it acquires immune suppressive properties. It is a convention among immunologists to characterise an mDC by the expression of membrane molecules such as CD80, CD83, or CD86. However, in contrast to IL-12 that reaches maximum expression within a few hours and is lost after 24 hours, these membrane molecules reach their maximum expression only after 48 hours. In order to clearly distinguish the IL-12 secreting DCs that are described herein from what is conventionally understood by the name mature DC, the term semi-mature DCs was chosen. This, very importantly, shall not imply some kind of functional deficiency but only a certain differentiation stage at the time kinetic scale in FIG. 1. The smDC is functionally different from an iDC as well as from an mDC.

WO 2007/117682 relates to mature dendritic cells which are transfected with mRNA molecules encoding for CD40L.

Koya R. C. et al. (J Immunoth. 26 (2003):451-460) describe the transfection of immature dendritic cells with viruses coding for CD40L. CD40L is required to mature these dendritic cells.

In Liu Y. et al. (Cancer Gene Therapy 9 (2002):202-208) the transfection of immature dendritic cells with viruses encoding CD40L is disclosed.

It is an object of the present invention to provide a method for producing dendritic cells based on genetic engineering. These dendritic cells may be used to prepare pharmaceutical preparations.

The present invention relates to a pharmaceutical preparation comprising partially matured dendritic cells obtainable by a method comprising the steps of:

a) providing immature dendritic cells or precursor cells thereof or partially matured dendritic cells obtainable by contacting immature dendritic cells with at least one dendritic cell maturation agent to produce partially matured dendritic cells (semi-mature DCs, smDCs) as defined by their capacity to secrete IL-12, b) manipulating the cells of step a), in particular the partially matured dendritic cells (semi-mature DCs, smDCs) releasing IL-12 of step a), to (i) over-express at least one immune molecule capable of maintaining the T-lymphocyte stimulatory capacity of dendritic cells characterised by continued IL-12 secretion for at least 24 hours, preferably at least 48 hours, and selected from the group consisting of CD40L by introducing nucleic acid molecules encoding for said at least one molecule; and/or (ii) inhibit or prevent the expression of at least one T-lymphocyte suppressive molecule acting within dendritic cells exposed to a primary maturation agent such as LPS/IFN-γ or being released from dendritic cells exposed to a primary maturation agent such as LPS/IFN-γ and being selected from the group consisting of interleukin 10 (IL-10), and indoleamine 2,3-dioxygenase (IDO), such as at least one of the genes given in the tables 3, 4 and/or 5, by knocking out the gene or a fragment thereof encoding said at least one T-lymphocyte suppressive molecule or by introducing nucleic acid molecules, preferably ribonucleic acid molecules, to inhibit or prevent the expression of the at least one T-lymphocyte suppressive molecule that is active within the dendritic cell or is delivered from the dendritic cells to T-cells and c) optionally adding substances to transform precursor cells of dendritic cells into dendritic cells.

The pharmaceutical preparation according to the present invention comprises dendritic cells obtainable by the methods disclosed herein. The dendritic cells that are subjected to genetic engineering aim at over-expression of molecules contributing to immune stimulation such as CD40L, or genetic engineering aimed at knocking down the expression of immune suppressive molecules such as IL-10 or IDO, and the newly identified molecules listed in tables 3, 4 and 5 below, which show an expression kinetic in DCs that is similar to IL-10 and IDO. The genetic engineering may be performed on any DCs or precursor cells, like hematopoietic stem cells, no matter whether these dendritic cells are exposed to a maturation agent such as a TLR ligand, a cocktail of inflammatory cytokines, or T-cell derived signals such as a CD40L mediated signal, or subjected to another procedure aimed at triggering the phenotypic switch from an immature to a mature DC, or they may be at an immature stage. The (genetic) manipulation may be performed before or after the exposure to a maturation stimulus. It is preferred to apply the maturation stimulus (or a combination of maturation stimuli) for a brief period of time only, e.g. for no longer than 24 hours, 12 hours, but especially preferred for 6 hours, but also for less than six hours. The favoured application of a brief (at least 2 hours) maturation stimulus to the DCs assures that a DC immune medicine after inoculation into a patient has retained the capacity for high efficiency initiation of T-cell stimulation. The genetic engineering of the DCs aims at improving that basic immune stimulatory capacity but is not intended to replace it.

Precursor cells of dendritic cells employed for the production of the dendritic cells of the pharmaceutical preparation of the present invention have to be transformed into dendritic cells. Means and methods to achieve this are known in the art. "Precursor cells of dendritic cells" include monocytes, hematopoietic cells etc.

Another aspect of the present invention relates to a method for producing dendritic cells comprising the steps of:

a) providing immature dendritic cells, b) contacting said immature dendritic cells with at least one dendritic cell maturation agent to produce partially matured dendritic cells (semi-mature DCs, smDCs) as defined by their capacity to secrete IL-12, and c) manipulating the partially matured dendritic cells (semi-mature DCs, smDCs) releasing IL-12 of step b) to (i) over-express at least one immune molecule capable of maintaining the T-lymphocyte stimulatory capacity of the dendritic cells characterised by continued IL-12 secretion for at least 24 hours, preferably at least 48 hours or longer, and the at least one immune molecule being selected from the group consisting of CD40L by introducing nucleic acid molecules encoding for said at least one molecule; and/or (ii) inhibit or prevent the expression of at least one T-lymphocyte suppressive molecule acting within the dendritic cell exposed to a primary maturation agent such as LPS/IFN-γ or being released from dendritic cells exposed to a primary maturation agent such as LPS/IFN-γ and being selected from the group consisting of interleukin 10 (IL-10), and indoleamine 2,3-dioxygenase (IDO), such as at least one of the genes given in the tables 3 & 4, by knocking out the gene or a fragment thereof encoding said at least one T-lymphocyte suppressive molecule or by introducing nucleic acid molecules, preferably ribonucleic acid molecules, to inhibit or prevent the expression of the at least one T-lymphocyte suppressive molecule that is active within the dendritic cell or is delivered from the dendritic cells to T-cells.

Genetically engineered IL-12 releasing DCs of step b) of the methods described above over-express at least one molecule capable of extending the T-lymphocyte stimulatory time window and/or entirely preventing its closing after 24 hours characterised by maintained secretion of longer than 24 hours by introducing nucleic acid molecules encoding for said at least one immune stimulatory molecule; or show an inhibited or down-regulated expression of at least one molecule that is involved in the normal developmental progress of a DC after exposure to any effective maturation stimulus from the T-lymphocyte stimulatory into a T-lymphocyte suppressive time window that starts opening 24 hours after maturation; and/or inhibit or prevent the expression of at least one molecule that fulfils a function in mediating T-lymphocyte suppression by DCs that have developed to assume an immune suppressive phenotype. This is accomplished by knocking out the gene or a fragment thereof encoding said at least one molecule and/or by introducing nucleic acid molecules, preferably ribonucleic acid molecules, to inhibit or prevent the expression of at least one molecule that interferes with the normal development of DCs after exposure to a maturation stimulus from an immune stimulatory to an immune suppressive phenotype; and/or interfering with signals that are delivered from the DC to the T-cells causing suppressing the activity of this T-cell and thus suppressing an immune response. The dendritic cells of the present invention maximise T-lymphocyte stimulation, particularly CTL activation by using genetic engineering to broaden the stimulatory time window of approximately 24 hours or entirely prevent closing of this stimulatory time window after 24 hours. Alternatively to IL-10 or IDO, other molecules that are involved in the immune suppressive function of the DCs that starts approximately 24 hours after exposure to any maturation stimulus (table 3, 4, and 5) may be used. It will be these molecules that are preferably targeted in the manufacturing of genetically engineered immune stimulatory DCs. It is particularly preferred to use molecules that show a two-fold over expression in the presented DNA micro array data (table 3 and 4), more preferable an over-expression of at least six fold. The numbers given in tables 3 & 4 show the fold over-expression as indicated in the heading of the respective column. It is particularly preferred to knock down the expression in a DC immune medicine of the molecules that appear to be involved in immune suppression, as demonstrated in the example depicted in FIG. 9.

By reversing the strategy outlined above it is possible to design a genetically engineered T-lymphocyte suppressive DC immune medicine for the treatment of pathological overactivity of the immune system, e.g. in allergies or autoimmune diseases, as well as in stem cell and organ transplantation. Immune suppression is physiologically mediated by a DC that has differentiated for more than 24 hours after exposure to any maturation stimulus. The immune suppressive capacity of such a DC is enhanced by interfering with the expression of T-lymphocyte stimulatory molecules during the first 24 hours of DC differentiation; and/or by over-expressing molecules that confer T-lymphocyte suppression by genetically engineering the DC according to the strategies outlined above.

The use of smDCs as a target for genetic manipulation is a central and critical part of the present invention. The immune stimulatory effects of mDCs that were published in the past are mainly due to the highly artificial experimental setting in which many of these experiments were performed, for example the use of synthetic peptides, which do not exist in nature, instead of the real targets of DCs: native protein antigen molecules or even whole cells, both of which require completely different mechanisms of uptake and processing by DCs. Many other investigators used the murine system for their research and there are critical differences between humans and mice that cause much confusion. However, it is now generally accepted that mDCs have immune suppressive properties. It surprisingly turned out that dendritic cells obtained with the method according to the present invention exhibit a broader stimulatory window (i.e. increased and prolonged expression of IL-12). It was found that genetic engineering of a semi-mature (sm) DC—a DC in which the physiologic differentiation process is initiated by exposure to any maturation stimulus capable of triggering IL-12 secretion from DCs, but which, however, is removed preferably after two to twelve hours, more preferably after six hours—to over-express the CD40L molecule has the capacity to maintain its T-lymphocyte stimulatory capacity for at least 24 hours, preferably 48 hours, and even up to five or even ten days. It is furthermore preferred to culture such genetically engineered DCs in medium containing IFN-γ. Such DCs render smDCs by a typically six hour-exposure to a Toll-like receptor (TLR) ligand, preferably but not exclusively lipopolysaccharide (LPS), again preferably in the presence of IFN-γ, —see Table 1—and genetically engineered to over-express CD40L, assume a phenotype that is characterised by continued secretion of IL-12 for at least one, preferably three, and even up to five days and the maintenance of the immune stimulatory capacity in an allogeneic mixed leukocyte reaction (alloMLR) for at least 24 hours, preferably 48 hours, but up to five days. Applied to the design of a DC immune medicine, this confirms the existence of an early immune stimulatory and a later immune suppressive window of DC differentiation and associated function. The general principle in the development of stimulatory DC immune medicines may therefore be to broaden the early immune stimulatory window in order to more effectively trigger immune activation and reduce or close the later immune suppressive window, or vice versa for designing a suppressive DC immune medicine (FIG. 1).

In general, for producing of an immune stimulatory DC medicine ("DC immune medicine"; "immune medicine") for the treatment of, e.g., cancer or infectious diseases, an initial maturation stimulus such as LPS/IFN-γ needs to be applied to the DC in order to initiate the physiologic differentiation from iDCs into smDCs. Other TLR ligands (table 1) may serve the same purpose as LPS; combinations of TLR ligands may give a stronger but not a qualitatively different signal. If the stimulatory potential of a T-lymphocyte stimulatory DC immune medicine is based only on the artificial manipulation of the gene transfer without the initial exposure to a TLR ligand mediated maturation stimulus (e.g. by direct genetic engineering of immature DCs), important contributions to the DC function will be lost and the T-lymphocyte stimulatory DC immune medicine may not reach its full potential. A critical difference of the genetically engineered DC immune medicine according to the present invention to a DC immune medicine that is manufactured by only an exposure to a maturation agent or combinations thereof, e.g. LPS/IFN-γ (smDC), is that for the latter it is critical that the smDC immune medicine is applied during the corresponding brief window of DC differentiation. Such a stimulatory DC immune medicine has therefore to be applied early after exposure to the maturation stimulus, whereas the genetic engineering e.g. by over-expression of CD40L aims at broadening the immune stimulatory time window of DC differentiation allowing for a less time critical application but most importantly prevent the development of DCs from an immune stimulatory to an immune suppressive phenotype (FIG. 1). A comparable improvement of the immune stimulatory capacity of DCs may be accomplished by knocking down molecules suspected to be critically involved in immune suppression as indicated by an expression profile that is similar to the expression of the known immune suppressive molecules IL-10 or IDO (listed in FIGS. 3, 4 and 5); or molecules that have already shown to be involved in immune suppression, as knocking them down in DCs resulted in improved T-cell stimulatory capacity of engineered DCs (FIG. 9). Also, the immune stimulatory time window of the older smDC immune medicine closes after 24 hours, whereas the novel genetically engineered DC immune medicine will maintain its T-lymphocyte stimulatory potential for at least one, preferably three, but up to five days longer. A comparable concept holds true for a T-lymphocyte suppressive DC immune medicine. The immature DCs first need to be exposed to a conventional maturation stimulus, such as LPS/IFN-γ, in order to initiate differentiation towards an mDC phenotype corresponding to the T-lymphocyte suppressive window of DC differentiation. The genetic engineering to over-express T-lymphocyte suppressive molecules from the DC immune medicine may be done before maturation of immature DCs by a maturation stimulus such as LPS/IFN-γ, but also when targeting precursor cells of DCs such as monocytes from the peripheral blood, or haematopoietic stem and precursor cells, especially but not exclusively when gene transfer methods are used that result in stable integration into the genome such as retroviral gene transfer. In addition to genetic engineering before exposure to the maturation stimulus, the genetic engineering may be done six hours and up to 48 hours after initiation of maturation by e.g. LPS/IFN-γ. When immature DCs are genetically engineered to over-express immune-suppressive molecules, important contributions by the physiologic T-lymphocyte suppressive activity of DCs longer than 24 hours after exposure to a maturation stimulus would be lost, for which reason we prefer the genetic engineering of DCs only in combination with the exposure of these DCs before (even at a precursor cell level) or after the genetic engineering to a maturation stimulus such as LPS/IFN-γ. Without genetic engineering of a T-lymphocyte suppressive DC immune medicine, the application of such a suppressive DC immune medicine has to be done during that suppressive window of DC differentiation whereas a T-lymphocyte suppressive DC immune medicine genetically engineered to over-express molecules that mediate suppression of T-lymphocyte activity allows for a much more flexible administration to the patient.

TABLE 1

TLR ligands

| Receptor | Naturally occurring | Synthetic analogues | Fully synthetic small molecules |
|---|---|---|---|
| Exogenous ligands | | | |
| TLR1 | Not determined | Triacyl lipopeptides | — |
| TLR2 | Lipoproteins/lipopeptides Peptidoglycan Lipoteichoic acid Lipoarrabinomannan Atypical lipopolysaccharide | Di- and triacyl lipopeptides | — |
| TLR3 | Double-stranded RNA | PolyI:C | — |
| TLR4 | Lipopolysaccharide HSP60 (Chlamydia pneumonie) | LPS/lipid A mimetics, such as MLP | Synthetic lipid A, E5564 |
| TLR5 | Bacterial flaggelin | Discontinuous 13-aminoacid peptide | — |
| TLR6 | Not determined | Diacyl lipopeptides | — |
| TLR7 | (G + U) rich single-stranded RNA (mouse only) | Oligonucleotides | Imidazole quinolines (imiquimod, resiquimod), guanosine nucleotides (loxoribine) |
| TLR8 | (G + U) rich single-stranded RNA (human only) | — | Imidazole quinolines (imiquimod) |
| TLR9 | Bacterial DNA Viral DNA Other DNA with non-methylated CpG sequences | CpG oligonucleotides | — |
| Endogenous ligands | | | |
| TLR2 | HSP70 | — | — |
| TLR4 | HSP60 Oligosaccharides of hyaluronic acid | — | — |

By genetically engineering DCs which have also received an LPS/IFN-γ or similar maturation stimulus before or after genetic engineering, to over-express T-lymphocyte stimulatory molecules and molecules that prevent closing of the immune stimulatory window, a DC differentiation will be possible to broaden the immune stimulatory time window of DC differentiation. It was elected to demonstrate the feasibility of the present invention by using CD40L gene transfer, as the interaction of CD40 expressed from DCs and CD40L expressed from activated T-lymphocytes delivers a potent activation and maturation signal to DCs. Such experiments are preferably performed in the presence of IFN-γ, which is a critical co-factor in the maturation of DCs, and all experiments with CD40L transgenic cells reported in the examples were done in the presence of IFN-γ. The same principle as CD40L gene transfer may be applied to other molecules that confer improved stimulatory capacity to DCs. Alternatively, a T-lymphocyte suppressive DC immune medicine may be designed by knocking out the expression of molecules, such as CD40 or IL-12 or similar molecules, or by over-expressing molecules that confer T-lymphocyte suppression from the DC immune medicine.

By interfering with the expression and/or function of T-lymphocyte suppressive molecules, the immune suppressive window of DC differentiation may be closed or made narrower or moved to a later time point. The feasibility of this approach is demonstrated by knocking down the expression of molecules that interfere with T-lymphocyte activation by DCs. The improvement of T-lymphocyte function by knocking down DC-derived T-lymphocyte suppressive signals, as e.g. the enzyme IDO that metabolises tryptophan, on which activated T-lymphocytes heavily depend, into kynurenines that have pro-apoptotic effects on activated T-lymphocytes, is shown in the example section. As a second example the expression of IL-10 was targeted, which is considered the prototypic immune suppressive molecule and which is expressed by DCs during the immune suppressive differentiation time window. In order to knock down the expression of target molecules, RNA interference is preferably used, but other technologies, such as the intracellular expression of single chain monoclonal antibodies or anti-sense RNA, may serve the same purpose. Alternatively, over-expression of said molecules (e.g. IDO or IL-10) or similar molecules may serve to design a T-lymphocyte suppressive DC immune medicine on the basis of pre-matured smDCs. The results in the example section (FIG. 9) show that knocking down the expression of molecules that have an expression kinetic comparable to IL-10 and/or IDO also results in an improved T-cell stimulatory capacity of genetically engineered DCs.

The structure and properties of a DC need to be described in a dynamic fashion that takes into consideration the developmental stages of a DC. Each of these stages may be characterised by the absence or presence of certain marker molecules. This also indicates that the molecular features of a DC depend on the specific stage of differentiation of this DC and the conditions that caused a DC to assume a certain differentiation pathway. The developmental plasticity of a DC also explains why it is advantageous to use what is called a semi-mature type 1 DC (smDC1) ("T cell activating dendritic cells characterised by the release of interleukin 12"). To initiate the switch from the tolerance maintenance function to the immune stimulatory stage, the DC needs to be exposed to a maturation stimulus (dendritic cell maturation agent). This opens the immune stimulatory time window during which the DC most importantly releases IL-12 as a response to the combination of LPS and IFN-γ or similar reagents that are added to the DC manufacturing culture. IL-12 acts via a specific receptor on helper T-lymphocytes and causes them to assume a Th1 phenotype, resulting in the support of cytolytic immunity. In order to allow this DC/T-lymphocyte interaction and the development of cytolytic immunity the DCs are preferably inoculated into the organism (e.g. human) at an early time point during the immune stimulatory window. It is particularly preferred that said DCs are injected 6 hours after the maturation stimulus. Obviously, inoculation is associated with removal of the DC culture medium that contains the dendritic cell maturation agent (e.g. stimulatory molecules LPS and IFN-γ). A sufficiently sustainable signal is transmitted into the DC by a 2, preferably 4, more preferably 6-hour exposure to said maturation agents (e.g. LPS and IFN-γ) so that after said exposure the DC is irreversibly committed to complete the process of maturation and no longer depends on the presence of the ligands, i.e. DC maturation agents. Formally, however, at the time of application the DCs have not yet completed their maturation process, which takes 1-2 days. The smDC1 design takes optimal advantage of the immune stimulatory time window during the first 24 hours after initiation of maturation and before the immune suppressive time window opens and starts to down-modulate the immune response.

At an early phase after exposure to a maturation stimulus, such as LPS/IFN-γ, DCs possess strong immune activating properties (the activating window, FIG. 1), whereas at later stages of their development they enter an immune suppressive phase (the suppressive window, FIG. 1). Molecular mechanisms of T-cell activation are well studied and understood. The molecular nature of and the events initiating negative regulatory feedback loops are much less studied. Thus, the design of the DC immune medicine according to the present invention aims at broadening the immune stimulatory window for enhancement of the immune activation and down-scaling or closing the immune suppressive window, thus blocking negative regulatory feedback loops in DCs. This was accomplished by genetically engineering DCs either by over-expressing immune stimulatory genes in addition to exposing them to DC maturation agents before or after genetic engineering, such as LPS/IFN-γ, or by knocking down immune-suppressive genes using RNA interference. The expression of a multitude of immune stimulatory or immune suppressive genes may be modulated following the same basic principle. The feasibility of this approach by over-expressing the immune-stimulatory CD40L molecule or by knocking down the immune-suppressive molecules IL-10 and IDO is shown in the example section. Combinations of over-expression and knock down may enhance the potency of a DC immune medicine but follow the same basic logic. A T-lymphocyte suppressive DC immune medicine for the treatment of pathological over-activity of the immune system may be designed in analogy to the T-lymphocyte stimulatory DC immune medicine by genetically engineering a DC initially exposed to a maturation stimulus, such as LPS/IFN-γ, by genetically engineering the resulting smDCs to over-express immune suppressive molecules and/or knock down immune stimulatory molecules in the DC.

According to the novel T-lymphocyte stimulatory or suppressive DC immune medicine based on genetic engineering that is described in the present invention, partially matured smDCs are manipulated by introducing into said DCs nucleic acid molecules encoding the at least one immune stimulatory or immune suppressive molecule and/or nucleic acid molecules, preferably ribonucleic acid molecules (e.g. siRNA), to inhibit or prevent the expression of at least one immune suppressive or immune stimulatory molecule.

The expression of immune stimulatory as well as immune suppressive molecules in DCs may be influenced or induced by various methods, whereby it is preferred to modulate said expressions by introducing nucleic acid molecules as outlined above. For instance, the nucleic acid molecule transfer can be achieved with lentiviral gene transfer vehicles as well as liposome-mediated transfection. The same principle, however, will hold true when other viral vectors, such as retro viruses or adeno viruses, or non-viral vectors, such as gene gun or poly-cationic technologies, or when any other gene transfer is/are employed.

Several strategies have been developed to introduce foreign genes into cells, including direct injection of plasmids or DNA liposome complexes and infection with modified viruses. However, safety and efficacy are important considerations in the development of therapy protocols that use such gene transfer methods. For example, proteins that are therapeutic in the context of one tissue may be harmful in another. Accordingly, transcriptionally targeted vectors that can restrict the expression of a therapeutic sequence to appropriate cells are particularly desirable. Furthermore, in some cases there may be a therapeutic window for certain proteins, such that levels of expression below or above certain thresholds may be ineffective or toxic, respectively. Therefore, it would also be desirable to create constructs and devise methods that allow exogenous control of expression, so that levels of a therapeutic protein can be raised or lowered according to therapeutic need.

Conventional viral and non-viral based gene transfer methods can be used to introduce nucleic acids encoding the respective molecules into the DCs of the present invention or, alternatively, nucleic acids that inhibit transcription or translation of said molecules, such as siRNAs or anti-sense RNAs. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene delivery procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10): 1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994).

Small interfering RNA molecules can also be used. In mammalian cells, introduction of long dsRNA (>30 nt) often initiates a potent antiviral response, exemplified by non-specific inhibition of protein synthesis and RNA degradation. The phenomenon of RNA interference is described and discussed, e.g., in Bass, Nature 411:428-29 (2001); Elbahir et al., Nature 411:494-98 (2001); and Fire et al., Nature 391:806-11 (1998), where methods of making interfering RNA also are discussed. The siRNAs sequences used in the present invention are preferably less than 100 base pairs, typically 30 bps or shorter, and are made by methods known in the art. Exemplary siRNAs according to the invention could have up to 29 bps, 25 bps, 22 bps, 21 bps, 20 bps, 19 bps, 15 bps, 10 bps, 5 bps or any integer thereabout or therebetween.

According to a preferred embodiment of the present invention, the precursors for the manufacturing of immature DCs are obtained from skin, spleen, bone marrow, thymus, lymph nodes, umbilical cord blood or, most preferably, from peripheral blood. The DCs used in the method according to the present invention can be directly isolated from a respective source or derived from progenitor cells. The person skilled in the art knows respective methods. For example, DC precursors and immature DCs can be isolated by collecting anti-coagulated peripheral blood, haematopoietic stem cells, by leukocyte apheresis, or by preparation of buffy coats, rosetting, centrifugation, density gradient centrifugation (e.g., using Ficoll (such as FICOLLPAQUE™), PERCOLO (colloidal silica particles (15-30 nm diameter) coated with non-dialyzable polyvinylpyrrolidone (PVP), sucrose, and the like), differential lysis of cells, filtration etc. In certain embodiments, a leukocyte population may be prepared, such as, for example, by collecting blood from a subject, defibrinating it, removing the platelets, and lysing the red blood cells. DC precursors, monocytes, or myeloid progenitor or stem cells may be used to differentiate iDCs. Monocytes can optionally be enriched from peripheral blood by, for example, taking advantage of their capacity to adhere to plastic surfaces, centrifugation through a density gradient, monoclonal antibody panning, counter flow centrifugation and the like. If the DCs obtainable by the method according to the present invention are used to treat individuals, the iDCs can be obtained from the individual to be treated or from a healthy individual HLA-matched to the individual to be treated.

DC progenitors can be cultured and differentiated in suitable culture media. Suitable tissue culture media include e.g. RPMI 1640 and DMEM. The tissue culture media can be supplemented with human autologous or pooled donor serum but not serum of any bovine source, amino acids, vitamins, cytokines, such as GM-CSF and IL-4 or IL-13, or IFN-γ, and divalent cations to promote differentiation of the cells. The progenitor cells may be preferably cultured also in serum-free clinical grade media. A typical cytokine combination used with dendritic cell culture medium comprises GM-CSF and IL-4 or IL-13, or IFN-γ.

In order to apply the maturation stimulus to the DCs that drives them into the smDC differentiation status (before or after genetic engineering or at the stage of a DC precursor cell such as a monocyte or a haematopoietic stem or precursor cell) that is the preferred status for a the DC immune medicine of the present invention, genetic engineering, an effective amount of at least one DC maturation agent is contacted with the iDCs. The at least one DC maturation agent is preferably selected from the group consisting of heat-inactivated or formalin-treated Bacillus Calmette-Guerin (BCG), preferably cell wall constituents of BCG, BCG-derived lipoarabidomannans or BCG components, lipopolysaccharide (LPS) derived from E. coli, or inactivated Gram positive or Gram negative microorganisms, an imidazoquinoline compound, preferably an imidazoquinoline-4-amine compound, in particular 4-amino-2-ethoxymethyl-x-dimethyl-1H-imidazol[4,5-c]quinolin-1-ethanol or 1-(2-methylpropyl)-1H-imidazo[4,5-c]quinolin-4-amine, or derivatives thereof (see e.g. WO00/47719), a synthetic double-stranded polyribonucleotide, preferably polyI:C, natural double-stranded RNA or RNA viruses or fragments of RNA, or synthetic analogues, or a synthetic or natural nucleic acid molecule comprising un-methylated CpG motifs. The majority of these compounds are TLR agonists (see table 1 for a comparison). In the present invention it is particularly preferred to use LPS as dendritic cell maturation agent. However, in principle, it is also feasible to use any TLR agonists alone or in combination with IFN-γ. In principle, it is also possible to expose iDCs to cocktails of cytokines for maturation that typically include but are not limited to tumour necrosis factor α (TNF-α), IL-1, IL-6, and prostaglandin E6, or parts of that combination. Furthermore, it is possible to trigger the CD40/CD40L signalling pathway. This may be done by contacting iDCs with recombinant CD40L molecules or fusion proteins comprised of the CD40L domain and another protein, such as IgG-Fc, in soluble form or immobilised at a surface, e.g. the culture dish or a nano-particle, or with primary cells or cell lines genetically engineered to express CD40L, or with activated T-lymphocytes that physiologically up-regulate expression of CD40L. The CD40/CD40L signal may be applied in any combination with TLR agonists, inflammatory cytokines. Of course any combination of at least two of said maturation agents may be used according to the present invention. The at least one (preferably at least 2, 3, 5, 10) dendritic cell maturation agent is preferably contacted with the dendritic cells in the presence of IFN-γ.

According to another preferred embodiment of the present invention, the iDCs prior to genetic engineering step c) are contacted with effective amounts of at least one dendritic cell maturation agent for at least 2 hours, preferably for at least 6 hours, in particular for at least 12 hours, and for a maximum of up to 24 hours. The maturation time depends on various parameters (e.g. DC maturation agent). The contact time and the other parameters have to be chosen so that the iDCs mature only partially into smDCs using methods known in the art. Cell surface markers can be detected in assays familiar to the art, such as flow cytometry and immunohistochemistry. The cells can also be monitored for cytokine production (e.g. by ELISA, another immune assay, or by use of an oligonucleotide arrays or protein arrays).

The at least one molecule capable of mediating maturation of iDCs into IL-12 releasing smDCs is preferably selected from the group consisting of LPS in the presence of IFN-γ in order to ready the DCs for the step of genetic engineering in order to manufacture a novel T-lymphocyte stimulatory or suppressive DC immune medicine with improved features. The at least one molecule capable of enabling the DCs to maintain their immune stimulatory phenotype characterised e.g. by the secretion of IL-12 beyond the physiologic immune stimulatory window of approximately 24 hours, thus conferring to them superior features in comparison with smDCs, is CD40L, typically but not necessarily in the presence of IFN-γ. We here elected to use an approach that is based on enabling smDCs to artificially express CD40L, which they normally don't, using genetic engineering methods outlined above. It is, however, conceivable, to express CD40L not from the DC itself but rather from an accessory primary cell or cell line, an activated T-lymphocyte, or to use soluble or immobilised recombinant CD40L molecules or fusion proteins. According to another preferred embodiment of the present invention, the at least one molecule that interferes with the expression of DC molecules that mediates T-lymphocyte suppressive activity is selected from the group consisting of interleukin 10 (IL-10) and indoleamine 2,3-dioxygenase (IDO). The molecule that mediates T-lymphocyte suppressive activity may also be selected from the molecules listed in tables 2 and 3 of the example section, whereby molecules showing two-fold over-expression in the DNA micro array expression profiling data are preferred, but molecules showing a six-fold or higher over-expression are particularly preferred.

According to a preferred embodiment of the present invention the at least one antigen is selected from the group
  a) consisting of tumour antigens, viral antigens, bacterial antigens, or any other human microbial or parasitic pathogens; or
  b) consisting of environmental antigens that cause allergy, auto-antigens against which an immune response was initiated that causes disease, or transplantation antigens.

In order to produce novel T-lymphocyte stimulatory or suppressive DC immune medicines with improved features based on smDCs, which are able to induce a specific enhanced immune response or enhanced immune suppression against an antigen in an individual, the iDCs are preferably loaded with at least one antigen before contacting them with the preferred LPS/IFN-γ stimulus to manufacture smDCs followed by genetic engineering. Antigen loading is necessary to instruct T-lymphocytes against what antigen they need to become active or which antigen they are supposed to tolerate. Antigens for the charging of DCs may be derived from diseased tissue, such as tumour antigen or viral antigens from virally infected cells. They may be a fragment of or an entire dead or living microorganism or a dead or living prokaryotic human or animal cell, e.g. a human or animal tumour cell. An antigen may be a recombinant protein, or a synthetic peptide, a DNA-based viral or non-viral recombinant expression vector or natural or synthetic RNA coding for an antigen. Alternatively, antigens may be environmental antigens that have triggered an immune dysfunction such as an allergy, an auto-antigen against which a pathologic autoimmune response has caused disease, or an antigen that determines organ or stem cell transplant rejection, such as MHC molecules. It is worth noting that, in case of a T-lymphocyte suppressive DC immune medicine for tolerance induction against an allogeneic transplant, loading might not be necessary, as the organ or stem cell donor DCs carry the same MHC molecules as the transplant. Obviously, in these latter situations a DC immune medicine will be designed in a way that it suppresses immunity against the allergen, transplantation antigen, or auto-antigen. In order to deliver the antigen to the DC, various methods may be used such as passive exposure that allows the DC to phagocytose the protein or peptide antigen, an antigenic protein complex, cells or cell membranes expressing antigens or antigenic peptides, texosomes, liposomes containing antigens or antigenic peptides, nucleic acids encoding antigens or antigenic peptides (possibly incorporated in plasmids or viral vectors), or total RNA from a tumour cell. These methods have been disclosed, for instance, in W099/03499. Such vehicles may be of viral or non-viral origin or may be nano-particles. Antigens may be tumour antigens, viral antigens, bacterial antigens, etc., more generally, any peptide or polypeptide against which an immune response or reaction is sought. In this respect, DCs may be sensitised to one or several antigens according to various techniques known in the art. The term "sensitized" indicates that the antigen or a portion thereof is exposed at the surface of the DCs, preferably in complex with molecules of the major histocompatibility complex (MHC). In principle, DCs could be inoculated into a patient without prior loading with an antigen and enabled for taking up an antigen in vivo, e.g. by injection directly into a tumour or into it's surroundings, into a metastasis, or into the draining lymphaytic system including lymph nodes and primary and/or secondary lymphoid tissue. Essentially, only the presence of the antigen and its presentation to a T-lymphocyte determines the DC immune medicine but not the way the antigen reaches the DC. An overview of DC loading techniques is given in R M Steinman & J Banchereau (Nature, Volume 449/27 September 2007, page 419-426) and the references therein.

The antigen-loaded and genetically engineered DC of the present invention may be used to therapeutically modulate immune responses in various immunological dysfunctions depending on the antigen loaded into said cells as well as the functional status the DC is in physiologically, by use of various signalling molecules such as DC maturation agents, or by genetic engineering of the DC. Such dysfunctions may include but are not limited to cancer, which may be pictured as a failure of the immune system to reject transformed and mutated cells; infectious disease, for example in the context of severe and otherwise untreatable microbial infections or in immune-compromised individuals, particularly during organ or stem cell transplantation. Other immune dysfunctions that may be treated by such a DC immune medicine may result from immunological hyper-activity, for example against environmental antigens resulting in allergies, or in situations where the immune system attacks its host causing autoimmune diseases. Finally, a DC immune medicine may be designed based on the methods of the present invention that interferes with the rejection of an organ or stem/precursor cell transplant including induced progenitor cells (iPS) generated by genetic engineering of other cells, thus facilitating the acceptance of the graft by its host. According to a preferred embodiment of the present invention, the at least one antigen is selected from the group consisting of tumour antigens, viral antigens, and bacterial antigens. The genetically engineered DCs according to the present invention may be loaded with any antigen against which an immune response in an individual should be induced, suppressed, or prevented. Particularly preferred are tumour antigens.

The novel genetically engineered DC immune medicine with improved T-lymphocyte stimulatory or suppressive capacity according to the present invention can be preserved, e.g. by cryopreservation either before maturation as iDCs, following partial maturation as smDCs, before or after genetic engineering as improved DCs prior to administration to a patient. Cryopreservation agents which can be used include but are not limited to dimethyl sulfoxide (DMSO), glycerol, polyvinylpyrrolidone, polyethylene glycol, albumin, dextran, sucrose, ethylene glycol, i-erythritol, D-ribitol, D-mannitol, D-sorbitol, i-inositol, D-lactose, choline chloride, amino acids, methanol, acetamide, glycerol monoacetate and inorganic salts.

A further aspect of the present invention relates to a pharmaceutical composition comprising the novel genetically engineered DC immune medicine with improved T-lymphocyte stimulatory or suppressive capacity according to the present invention. The DCs of the present invention can be formulated with physiologically acceptable carriers, excipients, buffers, and/or diluents using methods and compositions well known to the skilled artisan.

The novel genetically engineered DC immune medicine with improved T-lymphocyte stimulatory or suppressive capacity may be administered directly to a subject in need of immune modulation. Typically, about $10^2$ to about $10^{10}$ cells are suspended in a pharmaceutically acceptable carrier. If an individual suffering from cancer is treated, the cells are preferably injected into a disease free lymph node, preferably into the inguinal region but any tumour free or tumour bearing (metastatic) lymph node will serve the purpose, into the tumour directly or into a region, near to, adjacent to, or in circulatory or lymphatic contact with the tumour or tumour bed, or into metastatic disease. The DC immune medicine may be applied subcutaneously or intradermally into the skin to allow migration into lymph nodes. In principle, it is also possible to inject the DC immune medicine into the blood stream, either as a single shot or as an infusion over a longer period of time, into the peripheral blood or via a catheter into a blood vessel (artery or vein) that supplies a diseased organ or region of the body, or the portal vein or a pulmonary vein or artery, and the like. Implanted release devices may be used that deliver a continuous stream of the DC medicine into the tumour or a metastasis, a lymph node, the blood stream, or the skin.

The novel genetically engineered DC immune medicine with improved T-lymphocyte stimulatory or suppressive capacity of the present invention can be administered by any means appropriate for the formulation and mode of administration. For example, the cells can be combined with a pharmaceutically acceptable carrier and administered with a syringe, a catheter, a cannula, and the like. As above, the cells can be formulated in a slow release matrix. When administered in this fashion, the formulation can be administered by a means appropriate for the matrix used. Other methods and modes of administration applicable to the present invention are well known to the skilled artisan.

Compositions of the present invention can be used alone in the treatment of an individual, or the compositions can be used in combination with any other method to treat a tumour. For example, the methods of the present invention can be used in combination with surgical resection of a tumour; prior to, simultaneous with, or subsequent to radiation therapy and/or chemotherapy (cytotoxic drugs, apoptotic agents, antibodies, and the like); cryo-therapy; brachy-therapy; other forms of immune therapy (ex vivo expanded tumour antigen specific T-lymphocytes, NK cells, cytokines and growth factors, antibodies specific for tumour antigens, or targeting structures of the tumour tissue that are critical for tumour cell survival, such as blood vessels, etc.); gene therapy using viral or non-viral vectors, and the like. Furthermore, the DC immune medicine of the present invention can be co-administered with another agent, which agent acts as an adjuvant to the maturation of the dendritic cell and/or the processing of antigen within the tumour or region near or adjacent to the tumour. Any and all of these methods can also be used in any combination. Combination treatments can be concurrent or sequential and can be administered in any order as determined by the treating physician.

Another aspect of the present invention relates to the use of a dendritic cell according to the present invention for the manufacture of a medicament to treat and/or prevent cancer and/or microbial or parasitic infections; or to treat and/or prevent allergies, autoimmune disease, or stem cell or organ transplant rejection. The partially matured dendritic cells according to the present invention may be preferably employed in cancer prevention and/or cancer treatment. In such a case the dendritic cells are loaded with at least one tumour antigen. For example, but not by limitation, the cells can be administered directly into a tumour, into the tumour bed subsequent to surgical removal or resection of the tumour, peri-tumorally, into a draining lymph node in direct contact with the tumour, into a blood vessel or lymph duct leading into, or feeding a tumour or organ afflicted by the tumour, e.g., the portal vein or a pulmonary vein or artery, and the like.

The administration of the partially mature dendritic cells of the invention may be applied either simultaneous with or subsequent to other treatments for the tumour, such as chemotherapy or radiation therapy. Further, the partially mature dendritic cells of the invention can be co-administered with another agent, which agent acts as an adjuvant to the maturation of the dendritic cell and/or the processing of antigen within the tumour or region near or adjacent to the tumour. In addition, the dendritic cells can also be formulated or compounded into a slow release matrix for implantation into a region in or around the tumour or tumour bed such that cells are slowly released into the tumour, or tumour bed, for contact with the tumour antigens.

According to a preferred embodiment of the present invention the medicament is administered to an individual prior to, simultaneous with, or subsequent to radiation therapy and/or anti-tumour or anti-microbial chemotherapy, or any therapy aimed at treating allergies, autoimmune diseases, or stem cell or organ transplant rejection. The dendritic cells according to the present invention may be employed in combination with other cancer therapies in order to achieve an even more beneficial effect.

Another aspect of the present invention relates to the use of a dendritic cell according to the present invention for the manufacture of a medicament to treat and/or prevent immunological disease caused by a pathologic over-reaction of the immune system against environmental antigens, such as allergens, or against autoantigens in the course of an autoimmune disease.

Said medicament is preferably administered to an individual prior to, simultaneous with, or subsequent to other modalities aimed at treating or preventing allergies or autoimmune disease.

A further aspect of the present invention relates to the use of a dendritic cell according to the present invention for the manufacture of a medicament to treat and/or prevent the immunologic rejection of an allogeneic stem cell transplant, preferably used in the treatment of haematological malignancies, or to treat and/or prevent rejection of an allogeneic organ transplant.

Said medicament is preferably administered to an individual prior to, simultaneous with, or subsequent to other modalities aimed at treating or preventing the rejection of an allogeneic stem cell or organ transplant.

The present invention is further illustrated by the following figures and example, however, without being restricted thereto.

Figure 9A:
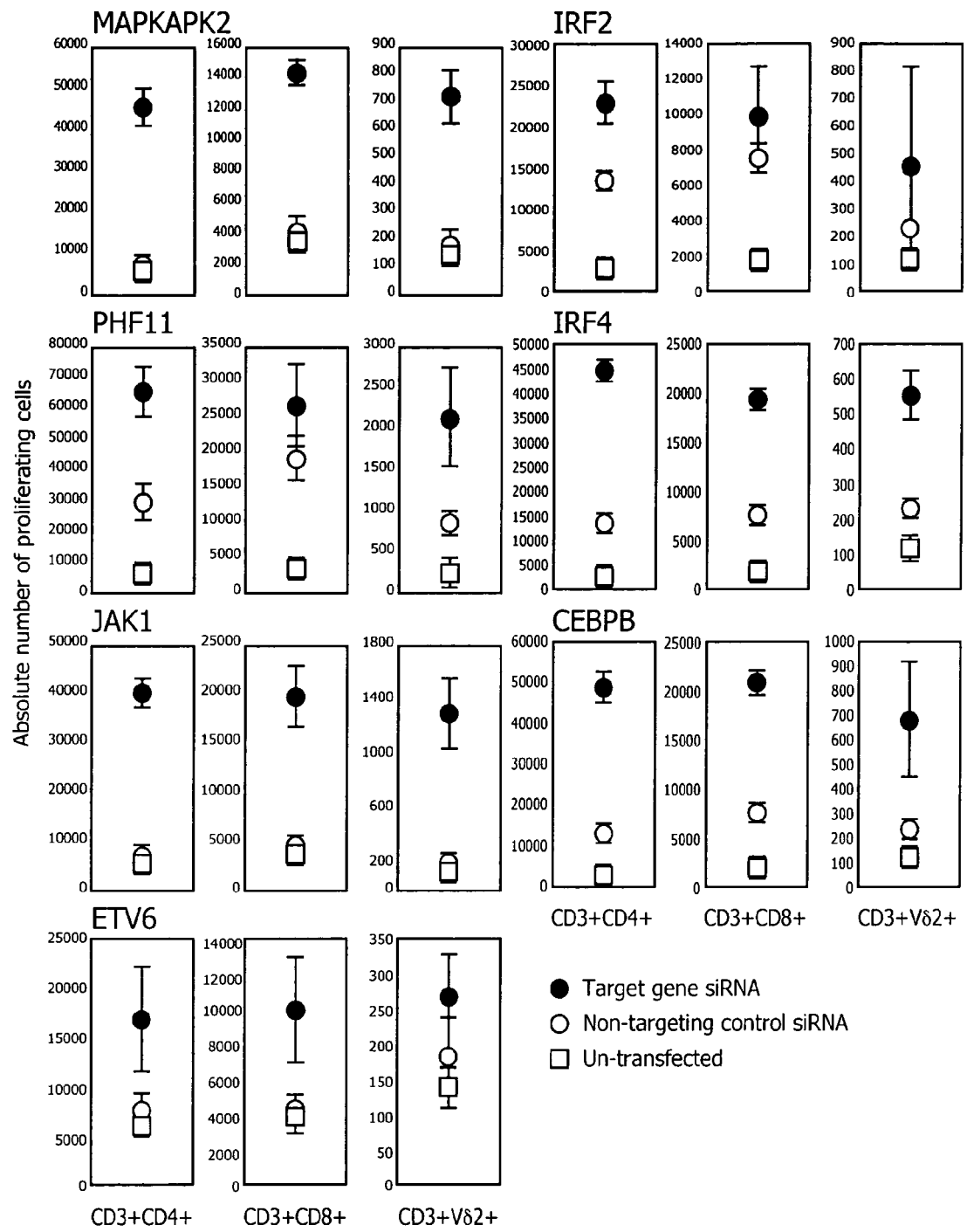
Figure 9B:
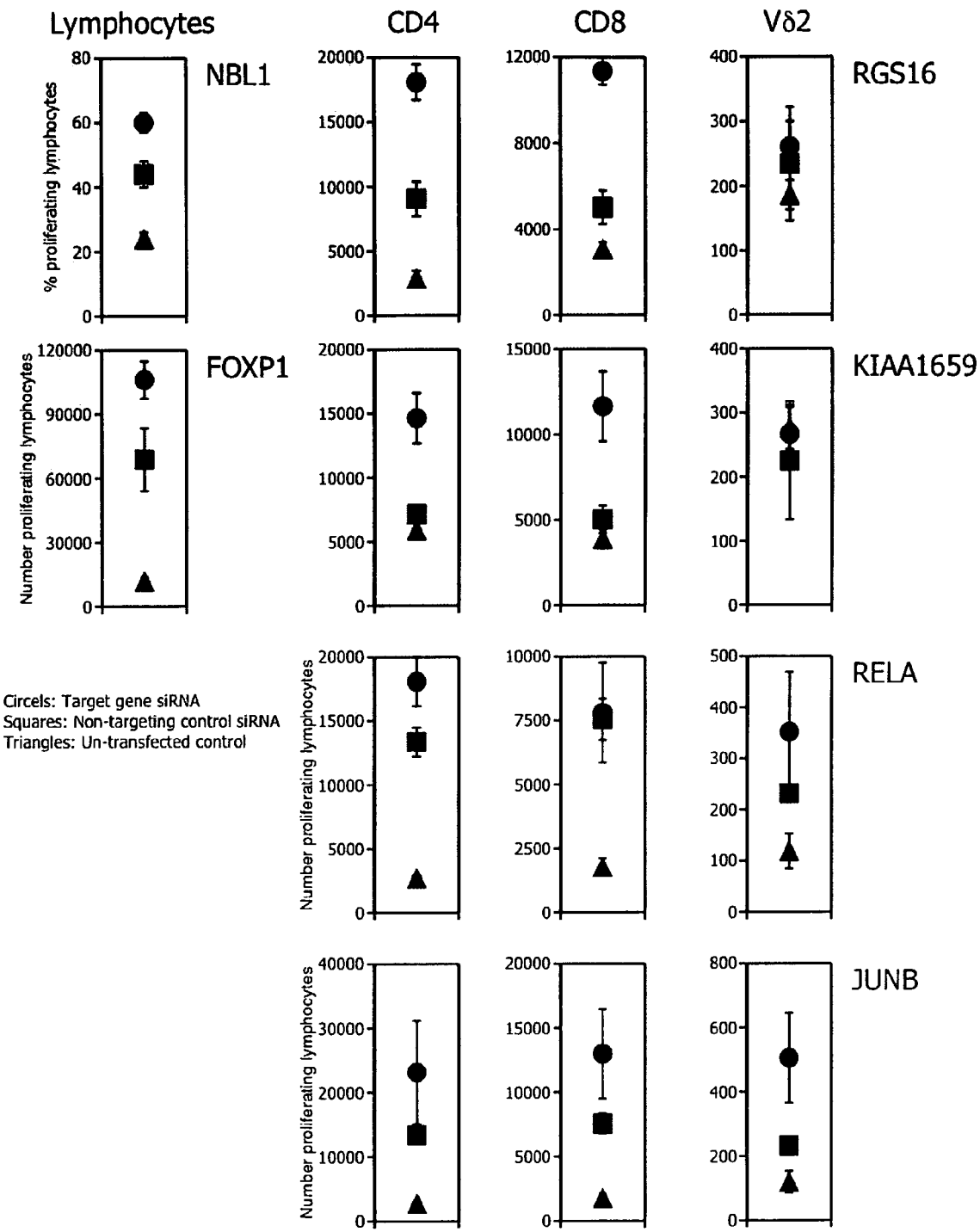

FIG. 9a shows examples for improved proliferative responses after knocking down the expression of target molecules in DCs identified in expression profiling experiments using RNA interference. FIG. 9b shows additional examples of genes that after knocking down their expression in DCs with siRNA result in an improved stimulatory capacity of such genetically engineered DCs for allogeneic lymphocytes as indicated compared to control siRNA transfection or untransfected DCs as indicated.

EXAMPLE

Method for Manufacturing a T-Lymphocyte Stimulatory or Suppressive DC Immune Medicine by Genetic Engineering Leukocyte Apheresis Leukocytes were collected using an Amicus leukocyte apheresis device (Baxter, Deerfield, Ill.) from healthy volunteers and patients suffering from various neoplasias treated in the context of clinical trials that were approved by the responsible institution's review boards. All individuals gave their informed consent to these studies according to the World Medical Association Declaration of Helsinki. Cell numbers and subsets were determined on a Sysmex cell counter (Sysmex, Bornbarch, Germany) and/or by flow cytometry.

Monocyte Enrichment

Monocytes were enriched by plastic adherence as described previously using AIM-V (Invitrogen, Carlsbad, Calif.) supplemented with 1% human pooled AB plasma (Octaplas, Octapharma, Vienna, Austria) or CellGro® medium (CellGenix, Freiburg, Germany). For the in-line procedures we followed the instructions provided by the manufacturers. Using the Elutra cell separator (Gambro BCT, Lakewood, Colo.), monocytes were enriched from the leukocyte apheresis product by loading into the elutriation chamber while maintaining the centrifuge speed at 2400 rpm. Thereafter, the centrifuge speed and the flow of elutriation media (PBS/I-ISA Baxter, New Jersey, N.J.) was held constant for cell fractionation. Alternatively, selection of monocytes was done with the CliniMACS® cell selection system (Miltenyi, Bergisch Gladbach, Germany) that uses CD14-coated magnetic beads to retain monocytes in a magnetic column. Another option for monocyte enrichment is depletion of T and B-lymphocytes for the enrichment of monocytes was done using the Isolex 300i Magnetic Cell Selector (Nexell, Irvine, Calif.). Lymphocytes were retained in a magnetic column by connecting them to CD2 and CD19 coated magnetic beads, and collecting the flow-through. The final products of all enrichment procedures were characterised by flow cytometry.

Flow Cytometry

Leukocyte apheresis and monocyte enrichment products were analysed for total leukocytes, T-lymphocytes, B-lymphocytes, monocytes, and granulocytes by antibody labelling with anti-CD45-FITC, anti-CD3-PerCP, anti-CD19-APC, anti-CD14-APC, and anti-CD15-FITC (BD Pharmingen San Diego, Calif.), respectively, using the Trucount system (Becton Dickinson, New Jersey, N.J.). Labelled cells were analysed on a FACSCalibur flow cytometer (Becton Dickinson, Mountain View, Calif.). The appropriate isotype control antibodies were included in the analysis.

DC Manufacturing

Monocytes isolated by the respective enrichment procedures described above were cultured at a density of $1 \times 10^6$ monocytes/cm$^2$ either in AIM-V medium supplemented with 2% pooled human AB plasma or in CellGro® medium at 37° C. in a humidified incubator for 6 days. The culture medium was supplemented with 1000 U/ml human GM-CSF and 300 U/ml human IL-4 (both from CellGenix, Freiburg, Germany) and replaced with the same volume of AIM-V/2% OP or CellGro® plus GM-CSF and IL-4 on day 3. Maturation was carried out on day 6 by adding 50 ng/ml IFN-γ (Boehringer Ingelheim, Vienna, Austria) and lipopolysaccharide (LPS, *E. coli* strain O111:B4, Calbiochem, San Diego, Calif., USA), ranging from 1-1000 ng/ml, to the culture for 6 hours to generate semi-mature (sm) DCs that subsequently were frozen; patient's DC vaccines were manufactured with clinical grade LPS (US Pharmacopeia, Bethesda, Md.).

DC Immune Phenotyping

The maturation status of the DCs was determined using the following antibodies: anti-CD86-APC (BD Pharmingen, San Diego, Calif.), anti-CD80-PE (Immunotech, Beckman Coulter, Fullerton, Calif.), anti-CD83-APC (all three from BD Pharmingen, San Diego, Calif.), anti-MHC I-PE, anti-MHC II-FITC (both from Dako Cytomation, Carpinteria, Calif.), and anti-CD45-PerCP (BD Pharmingen, San Diego, Calif.). The viability of the DCs was measured by propidium iodide staining (Sigma, St. Louis, Mo.). Cells were analysed using a FACS Calibur flow cytometer. The appropriate isotype control antibodies were included in the analysis.

IL-12 Detection by ELISA

IL-12 concentrations in the supernatant of the DC cultures were measured as described previously.

Allogeneic Mixed Leukocyte Reactions

Allogeneic responder PBMCs were isolated by gradient centrifugation from peripheral blood. Stimulating DCs (10000, 2000, or 400) were placed in triplicates with $10^5$ responder cells in 200 µl AIM-V medium supplemented with 2% pooled human plasma on a 96 well round bottom plate. For a positive reference, $10^5$ responder cells were stimulated with 100 ng/ml *Staphylococcal* enterotoxin A/B (SEA/SEB, Toxin Technologies Inc., Sarasota, Fla.). On day 4 the co-culture was incubated for another 18 hours with 1 µCi of tritium thymidine solution (NEN Life Science Products, Boston, Mass.). Finally, the cells were harvested with a Skatron (Lier, Norway) harvester. The incorporated tritium thymidine was counted using a Trilux-plate reader (Wallac Oy, Turku, Finland). Alternatively, allogeneic PBMCs were labelled with CFSE (Molecular Probes, Eugene, Oreg.) and mixed with DCs in a ratio of 1/5, 1/10, 1/20, 1/40, and 1/80. For the controls, no DCs or SEA/SEB was added. Finally, the PBMCs were labelled with anti-CD3-PerCP and analysed using a FACS Calibur flow cytometer. The percentage of CD3 positive CFSE negative T-lymphocytes was determined.

Lentiviral Gene Transfer into smDCs

Using ViraPower™ Lentiviral Expression System (from Invitrogen) lentiviral particles were generated by co-transfection of 293FT producer cell line with pLP-plasmids encoding for viral structural proteins, polymerase and reverse transcriptase (pLP/VSVG, pLP-1, pLP-2) and plasmids containing GFP or CD40L. 72 hours after co-transfection, the whole supernatant was harvested and 100× concentrated by ultracentrifugation. DCs were cultivated and matured under the conditions outlined above. DCs were harvested 48 hours or 6 hours after initiation of maturation, respectively. Pre-matured smDCs were then transduced with lentiviral particles (250 µl 100× concentrated lentiviral supernatant/$1 \times 10^6$ DC) in combination with 6 µg/ml Polybrene (from Sigma-Aldrich) plus IL-4, GM-CSF, and IFN-γ in standard concentrations. For IL-12 quality control supernatant was taken after 24 hours, and expression of GFP/CD40L was measured after 48 hours following standard procedures.

RNA Interference in DCs

DCs are manufactured according to the standard procedures outlined above. On day 6, $10^6$ DCs are transfected with 100 pmol gene-specific siRNA using a transfection reagent (Dharmacon) according to the manufacturer's instructions. Twelve hours after transfection, DCs are stimulated with LPS/IFN-γ for 6 hours. All uses are in analogy to the methods outlined above.

Results

Figure 1:
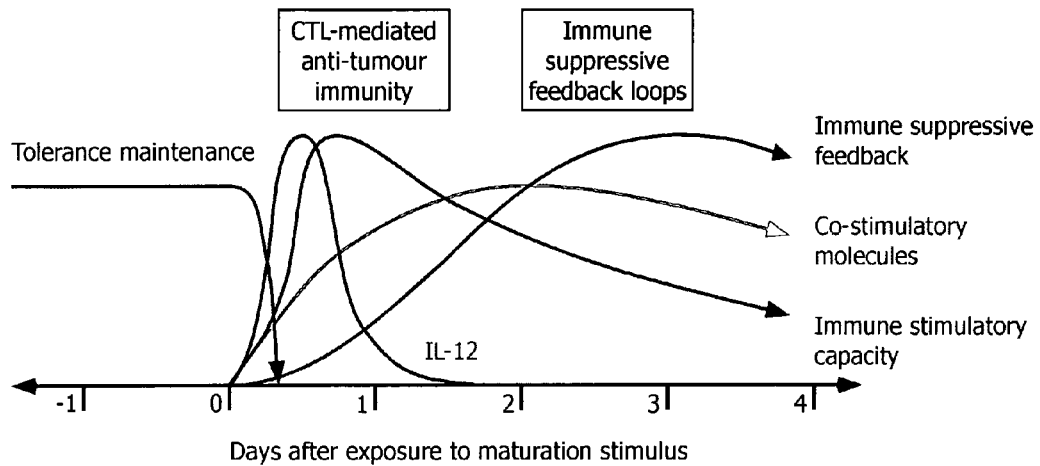
FIG. 1 shows developmental plasticity of a DC in a schematic representation of the kinetics of a DC differentiation process.

DC immune medicines currently in use employ monocyte-derived DCs that are charged with an antigen of any nature, as outlined in the introduction, and exposed to a maturation stimulus that has the capacity to trigger the release of IL-12 from the DC. A DC phenotype characterised by IL-12 secretion has the capacity to induce a type 1 polarisation of the immune system that supports cytolytic immunity. This implies that a stimulatory DC immune medicine needs to be applied to the patient during the time window of IL-12 secretion to allow presentation of the antigens from the DCs to the T-lymphocytes in the presence of IL-12 (FIG. 1). The novel genetically engineered DC immune medicine with improved T-lymphocyte stimulatory or suppressive capacity overcomes this limitation, as the genetic manipulations of the DCs allow the immune stimulatory window to remain open for a longer time period.

In the following examples, genetically engineered DC immune medicines have been manufactured and studied. Lentiviral gene transfer or liposome-based transfection to deliver DNA or RNA into DCs was used, but it may be assumed that any nucleic acid delivery technology may serve in that capacity. As an example of over-expression of an immune stimulatory gene in a DC immune medicine, DCs were engineered using lentiviral gene transfer to express the CD40L molecule. Functional studies confirmed that such an engineered DC immune medicine has an enhanced potential to stimulate immune responses. Furthermore, it is demonstrated that the knock down of the immune suppressive molecules IL-10 and IDO also enhances the stimulatory capacity by engineering DCs with siRNA molecules designed for RNA interference for IL-10 and IDO. In order to identify further DC molecules involved in immune suppressive feedback loops, whole genome DNA expression profiling using DNA micro arrays were conducted. Based on cluster analysis that grouped genes with an expression profile similar to that of IL-10 or IDO, a list of genes was found that has the potential to negatively regulate immune responses. Knocking down these genes in a DC immune medicine will thus improve its immune stimulatory capacity. Therefore, a DC immune medicine genetically engineered for allowing specific modulation of defined immune system components enables the treatment of associated immune system dysfunctions. Finally examples of the functional consequences of knocking down target genes expressed with kinetics similar to IL-10 or IDO in the DC expression profiling experiments using RNA interference are shown. In co-cultures with allogeneic T-lymphocytes an improved capacity of such genetically engineered DCs to trigger proliferation indicative for enhanced T-lymphocyte stimulation were observed.

Figure 2:
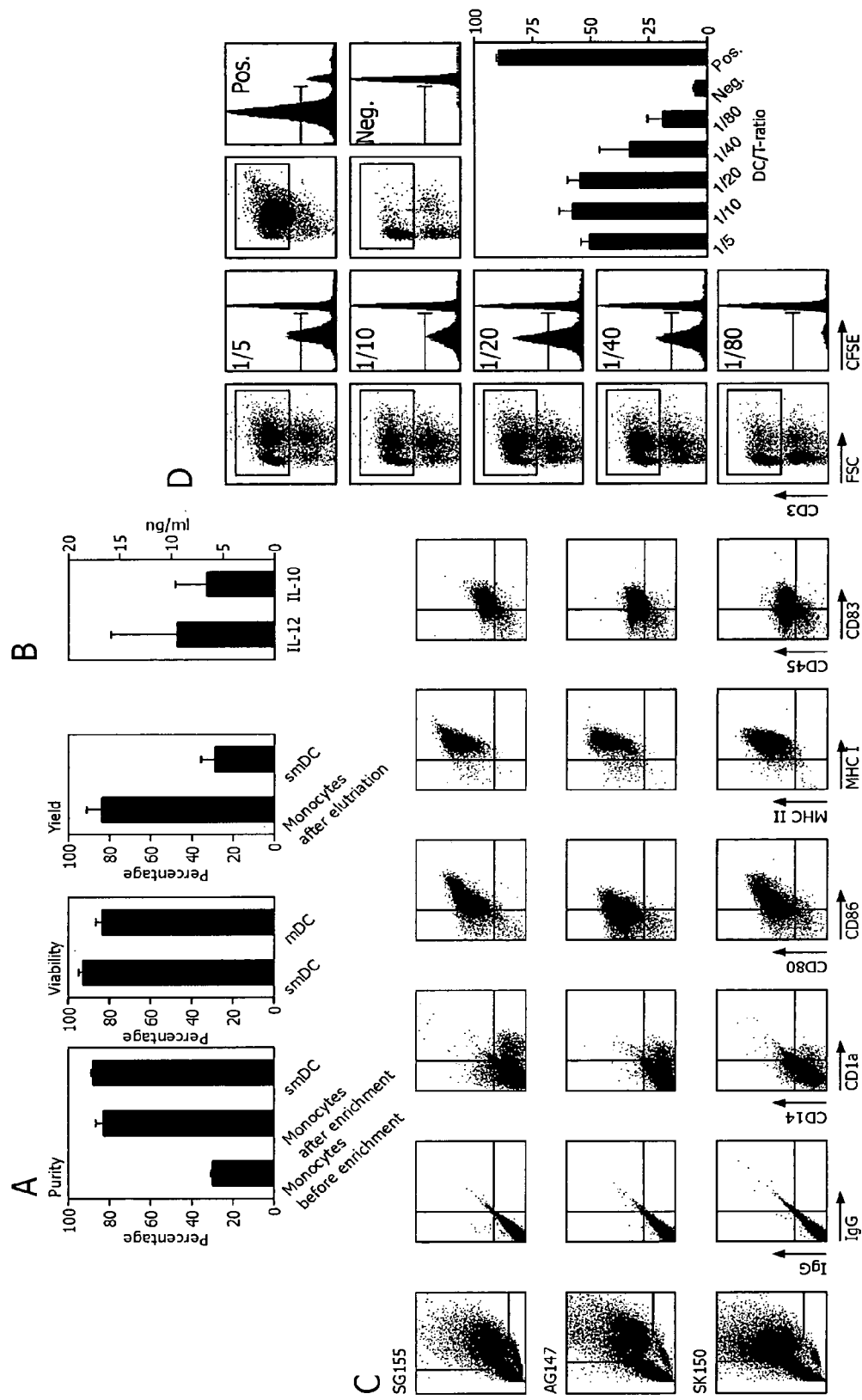
FIG. 2 shows a quality control of the smDC1 basic design.

FIG. 2 shows the quality control of the smDC1 basic design that is used for genetic engineering. The DC immune medicine has to meet defined quality control criteria. Panel A shows the purity, viability, and yield of DCs manufactured from peripheral blood monocytes. Such monocytes are collected by leukocyte apheresis, and monocytes are enriched by counter flow centrifugation (elutriation). In the presence of IL-4 and GM-CSF, monocytes differentiate in vitro within six days into iDCs. The iDCs are charged with antigen and subsequently exposed to a maturation stimulus comprised of LPS and IFN-γ for 6 hours and frozen. At this stage they are called semi-mature, as, although they are irreversibly committed to continue their maturation, they do not yet show the typical phenotypic and functional characteristics of mDCs. Most importantly, at that stage (the immune stimulatory window, approximately 0-24 hours after initiation of maturation, FIG. 1) DCs trigger immunity whereas at later stages (the immune suppressive window, approximately 24-48 hours after initiation of maturation, FIG. 1). However, in clinical application, they are injected into the patients at this differentiation stage where they complete their maturation and trigger immune responses (before 24 hours), but subsequently (at approximately 24 hours) also enter—according to their physiologic developmental program triggered by the maturation stimulus—an immune suppressive stage, which we aim to prevent by genetic engineering of the DC immune medicine.

For quality control, one aliquot of the DC immune medicine is thawed and re-cultivated for 2 days in order to let the DCs complete their maturation process. During these two days, they secrete cytokines, most importantly IL-12 (early after maturation) and IL-10 (late after maturation) (panel B; shown is mean±SEM from three individuals). Also, they show changes in the expression pattern of critical DC membrane molecules (panel C). Finally, DCs are subjected to an alloMLR potency test (panel D) by co-cultivation with CFSE-labelled allogeneic PBMCs at the indicated ratios, which triggers cell division that is associated with a dilution of the CFSE and a reduction of fluorescence. The bar graphs show the mean±SEM percentage of proliferating cells from three individuals.

The initial stimulus is also necessary for the initiation of the immune suppressive feedback loops. In general, the stronger the activation in response to a specific stimulus, the stronger the feedback signalling will be in order to down-modulate the immune activation to its baseline level, thereby preventing an immune response from getting out of control and causing auto-immune diseases. Thus, it was found that the maturation stimulus LPS/IFN-γ results in the highest amounts of IL-12 release, but also in the highest amounts of IL-10 release.

TABLE 2

Specifications of the basic design of smDC1 for cancer vaccination.

| Test | Specification | Test | Specification |
| --- | --- | --- | --- |
| Purity | 70-100% | IL-12 | >100 pg/ml |
| Viability | 70-100% | alloMLR | |
| Phenotype | | DC:MNC = 1:5 | >30% |
| CD80 | 60-100% | DC:MNC = 1:10 | >30% |
| CD86 | 60-100% | DC:MNC = 1:20 | >15% |
| MHC I | 60-100% | Negative control | <10% |
| MHC II | 60-100% | BACTEC | NEG |
| CD83 | 60-100% | Mycoplasma | NEG |
| CD14 | 0-40% | HIV 1/HIV 2 | NEG |
| IgG control | <1% | HBV/HCV | NEG |

Description of a Stimulatory DC Immune Medicine Enhanced Via Over-Expression of the CD40L Molecule.

Figure 3:
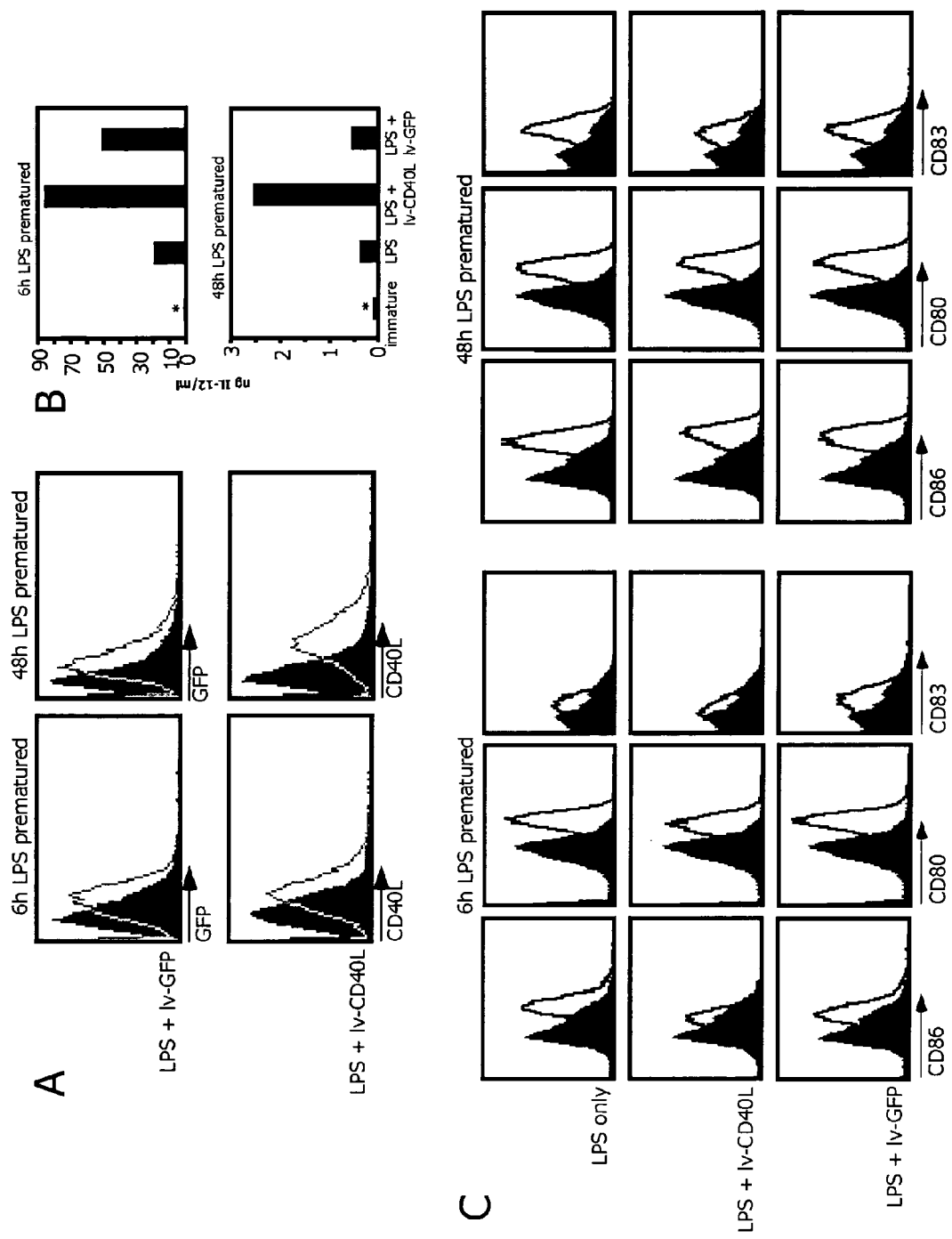
FIG. 3 shows the results of a CD40L gene transfer.

In order to broaden the immune stimulatory window of the DC that is characterised by the secretion of IL-12 (FIG. 1), DCs were genetically engineered to over-express CD40L. This molecule is normally expressed from activated T-lymphocytes and interacts with CD40 on DCs transmitting a critical activating signal into the DC. This experiment was designed as an example of the transfer of an activating molecule into the DC immune medicine. In principle, however, an identical procedure may be used for other stimulatory molecules or, in order to design a suppressive DC immune medicine, immune suppressive molecules may be over-expressed from a DC. Specifically, the rationale for CD40L gene transfer into DCs was (i) allowing the DCs to become independent from activating T-lymphocytes to deliver the CD40L signal to the DC;

(ii) it was hypothesised and found in the present experiments that, because of the continuous presence of CD40L on the DC itself by expression from a constitutively active promoter, the DC was enabled to secrete IL-12 for a much longer time period than when the DCs were subjected to a conventional maturation stimulus such as LPS/IFN-γ;

(iii) the total amount of IL-12 secreted from DCs was considerably higher compared to the LPS/IFN-γ or the CD40L/IFN-γ stimulus alone, and the kinetics of IL-12 secretion had been qualitatively different starting sooner after the stimulus was applied, thus broadening the immune stimulatory window of DC differentiation;

(iv) even 48 hours after exposure to LPS/IFN-γ, when the DCs had exhausted their capacity to secret IL-12, CD40L gene transfer enabled DCs to start a second phase of IL-12 secretion (FIG. 3).

FIG. 3 shows a CD40L gene transfer. In panel A the expression of GFP or CD40L after lentiviral gene transfer in 6 hours smDCs and 48 hours mDCs is shown. All measurements shown here were done 48 hours after exposure of pre-matured DCs to the lentiviral vector. Expression of CD40L from DCs caused enhanced secretion of IL-12 compared to iDCs, DCs exposed to LPS/IFN-γ alone, or GFP engineered 6 hours smDCs and 48 hours mDCs (panel B). The enhanced IL-12 release upon GFP gene transfer is probably caused by the viral double-stranded RNA that signals via TLRs (see table 1) that are expressed in 6 hour-smDC but not any more in 48 hour-LPS/IFN-γ mDCs. The expression profile of functionally important DC membrane molecules (panel C) was unaltered by lentiviral gene transfer into DCs (black histograms, immature DCs; white histograms, mDCs).

Figure 4:
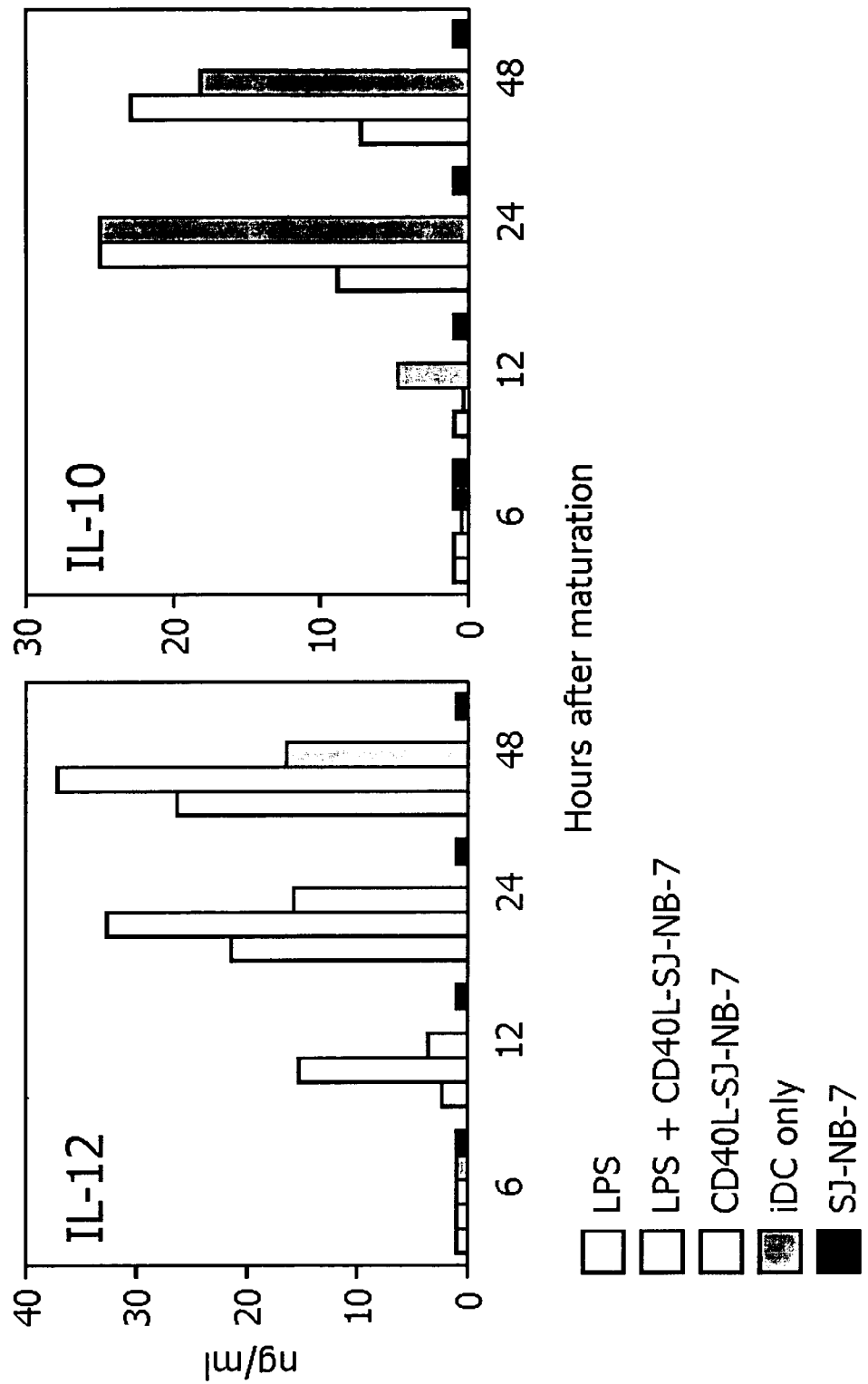
FIG. 4 shows the quantity and quality of IL-12 and IL-10 secretion.

The secretion of the cytokines IL-12 and IL-10 was qualitatively and quantitatively different in DCs that were exposed to LPS/IFN-γ, CD40L/IFN-γ, or a combination of both (FIG. 4). The secretion of IL-12 was almost twice as high when the combination stimulus was applied, compared to the CD40L/IFN-γ stimulus alone, and also considerably higher compared to the LPS/IFN-γ stimulus alone. In addition, IL-12 secretion from DCs exposed to the LPS/IFN-γ/CD40L combined stimulus was already clearly detectable at considerable amounts after 12 hours, whereas LPS/IFN-γ and CD40L/IFN-γ triggered biologically relevant levels of IL-12 secretion only between 12 and 24 hours after exposure to the initial maturation signal. This observation is in line with the goal of the present invention of broadening the immune stimulatory window of DC differentiation in order to improve the stimulatory capacity of a DC immune medicine. The maximum expression of IL-10 was similar when DCs were exposed to LPS/IFN-γ/CD40L or CD40L/IFN-γ alone, but was lower when only LPS/IFN-γ was used for DC maturation. However, the immune suppressive cytokine IL-10 was already detectable after 12 hours at biologically relevant levels after CD40L/IFN-γ signalling, whereas the combination stimulus LPS/IFN-γ/CD40L showed kinetics similar to those of only LPS/IFN-γ matured DCs. Early release of IL-10 as after CD40L/IFN-γ stimulation negatively interferes with the immune stimulatory window of DC differentiation and should, in the case of designing an immune stimulatory DC medicine, be avoided. It is concluded that the net effect in the balance between immune stimulatory and immune suppressive capacity of the combination stimulus LPS/IFN-γ/CD40L, considering the secretion pattern of IL-12 and IL-10, is clearly towards improved immune stimulatory capacity compared to applying LPS/IFN-γ or CD40L/IFN-γ alone. As opposed to earlier publications the DCs used here will receive a combination of maturation stimuli. Physiologically, a phase in which the DC can activate T-lymphocytes (characterised by IL-12 secretion) and a second phase, in which the DC will suppress the activity of T-lymphocytes (characterised by IL-10 secretion and tryptophan depletion by the activity of the enzyme IDO), will be triggered by contacting iDCs with an adequate maturation stimulus, such as LPS/IFN-γ (FIG. 1). Here it is demonstrated that the initial exposure to LPS/IFN-γ (or another TLR agonist in the presence of IFN-γ), followed by genetic engineering of the DCs to over-express molecules, such as CD40L maintains a DC phenotype capable of T-lymphocyte activation and prevents the DC from assuming the suppressive phenotype (FIG. 4). The secretion of IL-12 is maintained for longer than the physiologic time window of 20-24 hours when the genetic engineering is done 6 hours or 48 hours after the initial maturation via the TLR signalling pathway in the presence of IFN-γ.

FIG. 4 shows the quantity and quality of IL-12 and IL-10 secretion. DCs were exposed to the indicated maturation stimuli in the presence of IFN-γ. The concentrations of IL-12 and IL-10 in the culture supernatant were measured at the indicated time points.

Figure 5:
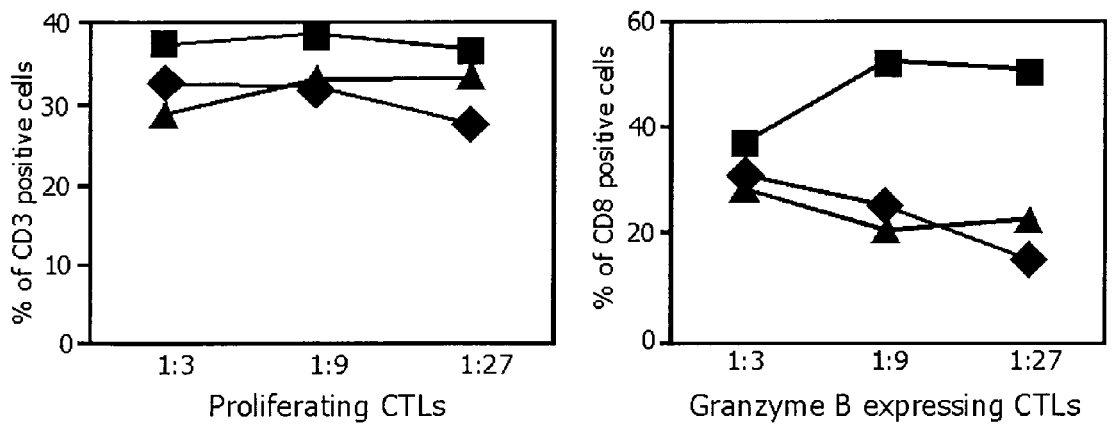
FIG. 5 shows the potential for cytolytic activity (square, CD40L transgenic DCs; diamond, GFP transgenic DCs; triangle, control DCs).

Of particular importance in the present design of a genetically engineered T-lymphocyte stimulatory DC immune medicine is that IL-12-secreting DCs have the capacity, via type 1 polarisation of an immune response, to trigger cytolytic immunity. Thus, the potential of T-lymphocytes exposed to CD40L transgenic DCs to trigger cytolytic immune responses by analysing the content of granzyme B in CD8 positive CTLs was further investigated (FIG. 5). Indeed, it was found that co-cultivation of CTLs with CD40L transgenic DCs resulted in clearly enhanced expression of granzyme B compared to control GFP transgenic DCs or un-transduced mDCs. This is a strong indicator of the improved cytolytic potential of such CTLs and thus provides evidence that CD40L expression from a DC immune medicine has improved immune stimulatory capacity.

FIG. 5 shows the potential for cytolytic activity. The total percentage of CTLs was only slightly increased when PBMCs were co-cultivated with CD40L transgenic DCs (left panel, squares) compared to GFP transgenic DCs (diamonds) and un-transduced mDCs (triangles). When analysing the granzyme B expression in CTLs co-cultivated with CD40L transgenic DCs, a clear increase was found (right panel, squares) compared to GFP transgenic DCs (diamonds) and un-transduced mDCs (triangles).

Description of a DC Immune Medicine with Improved Stimulatory Capacity for T-Lymphocytes by Engineering for Knocking Down the Expression of the Immune Suppressive Cytokine IL-10

Figure 6:
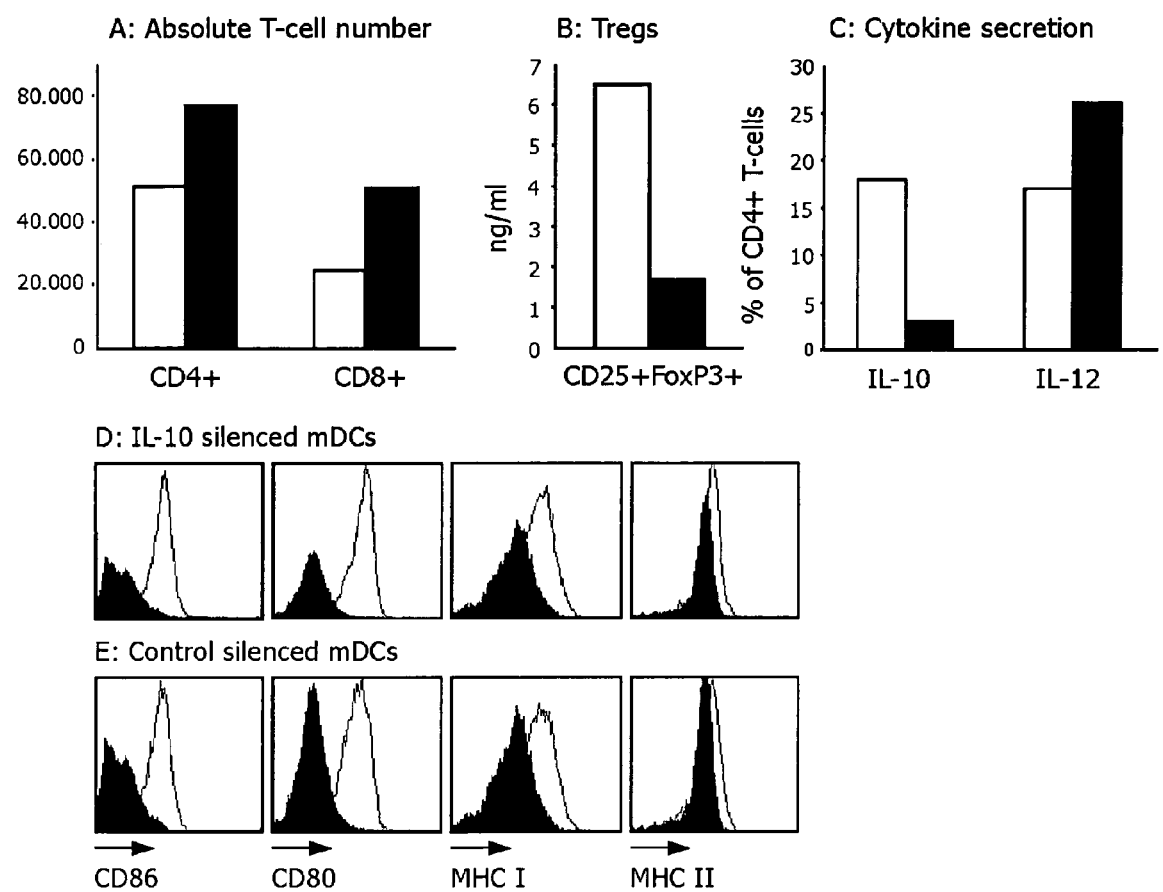
FIG. 6 shows the immune stimulatory capacity of LPS-activated DCs blocked for IL-10 expression.

Based on the hypothesis that a DC immune medicine in which the expression of molecules mediating immune suppression is knocked down, experiments were devised to block IL-10 gene expression in DCs by RNA interference using a pool of 4 target-specific siRNAs (FIG. 6). This resulted in very consistent and reproducible knock down of IL-10 expression in LPS/IFN-γ activated DCs, leading to a higher IL-12 secretion compared to control silenced mDCs. This observation hints at an autocrine pathway based on IL-10 secreted from a DC binding to IL-10 receptors on the same DC resulting in down modulated IL-12 production. Other than that, no immune phenotypic differences between genetically engineered and normal DCs, as assessed by CD80, CD86, MHC class I, and II expression, were found. Most importantly, in an alloMLR, a considerably greater potency of a DC immune medicine engineered for suppression of IL-10 secretion to activate T-lymphocytes compared to control experiments was observed.

Additionally, the percentage of CD25+FoxP3+ cells in the CD4+ T-cell population, supposedly a population of regulatory T-cells (Tregs) that suppresses immune responses, was reduced, probably due to the IL-10 silencing in LPS/IFN-γ activated DCs.

FIG. 6 shows the immune stimulatory capacity of LPS/IFN-γ-activated DCs, blocked for IL-10 expression by genetic engineering. Twelve hours before the activation with LPS/IFN-γ, DCs were transfected with a pool of four IL-10 specific siRNAs or an unspecific control siRNA. Isolated allogeneic CD3+ T-cells were then stimulated with 6 hour-LPS-matured DCs (mDCs) either IL-10 (black bars) or control-silenced (white bars) in a 1:3=DC:T-cell ratio. CD4+, CD8+, (panel A) and CD4+CD25+FoxP3+ T-cells (panel B) were analysed on day 6 of co-cultivation using the Trucount system and a FACS LSRII flow cytometer. The immune phenotype as well as IL-10 and IL-12 secretion were measured 48 hours after LPS/IFN-γ activation by flow cytometry and ELISA, respectively (panel C). The immune phenotypic analysis compares LPS/IFN-γ-activated DCs (white histogram) with iDCs (black histogram) in IL-10-silenced DCs (panel D) or control-silenced DCs (panel E).

Figure 7:
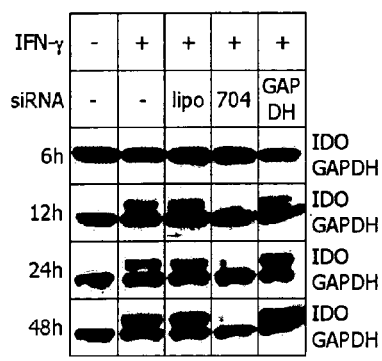
FIG. 7 shows the immune stimulatory capacity of LPS-activated DCs with silenced IDO expression.
Figure 7:
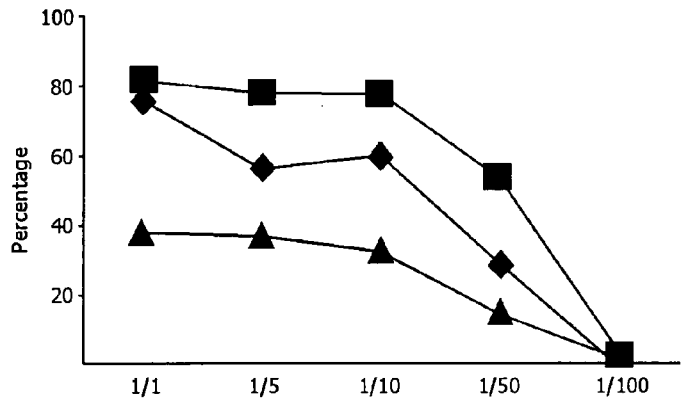
Figure 7:
Figure 7:
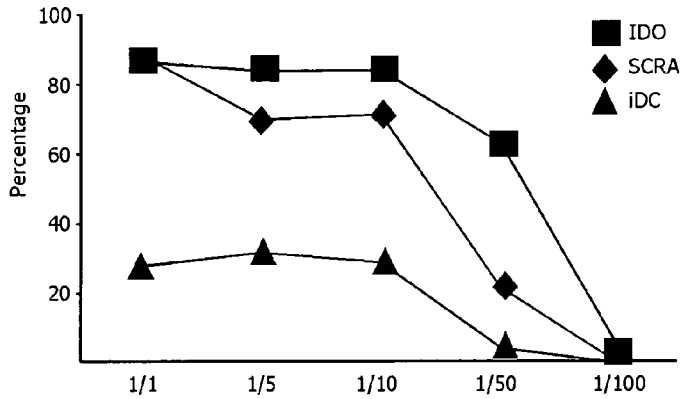

Description of a T-Lymphocyte Stimulatory DC Immune Medicine Engineered for Knocking Down the Expression of the Immune Suppressive Enzyme IDO siRNA was used to knock down the expression of the known immune suppressive effector molecule IDO (FIG. 7). In order to optimise the transfection of siRNA and the efficiency of IDO knock down, first HeLa cells, activated with IFN-γ, were used. Subsequently, DCs were transfected under optimised conditions. In both, HeLa cells and DCs, the expression of IDO as demonstrated in Western blot experiments could be silenced. IDO silenced DCs, DCs transfected with a scrambled control siRNA, and iDCs were used as stimulators in an alloMLR potency assay. It was observed that the stimulatory potency of IDO silenced DCs was considerably greater compared to DCs transfected with scrambled siRNA or iDCs. This held true for CD8+ CTLs as well as CD4+ Th-cells.

FIG. 7 shows the immune stimulatory capacity of LPS/IFN-γ-activated DCs with silenced IDO expression. First, efficient IDO knockdown in HeLa cells (panel A) as well as DCs (panel B) was demonstrated using Western blotting experiments. In order to investigate the stimulatory potency of IDO silenced DCs on CD8+ CTLs (panel C) and CD4+ Th lymphocytes (panel D), PBMCs were co-cultivated with IDO-silenced DCs (squares), control silenced DCs (diamonds, scra=sequence scrambled), or iDCs (triangles). In all cases the stimulatory capacity of IDO-silenced DCs was superior over the controls.

Immune Suppressive Molecules

Figure 8:
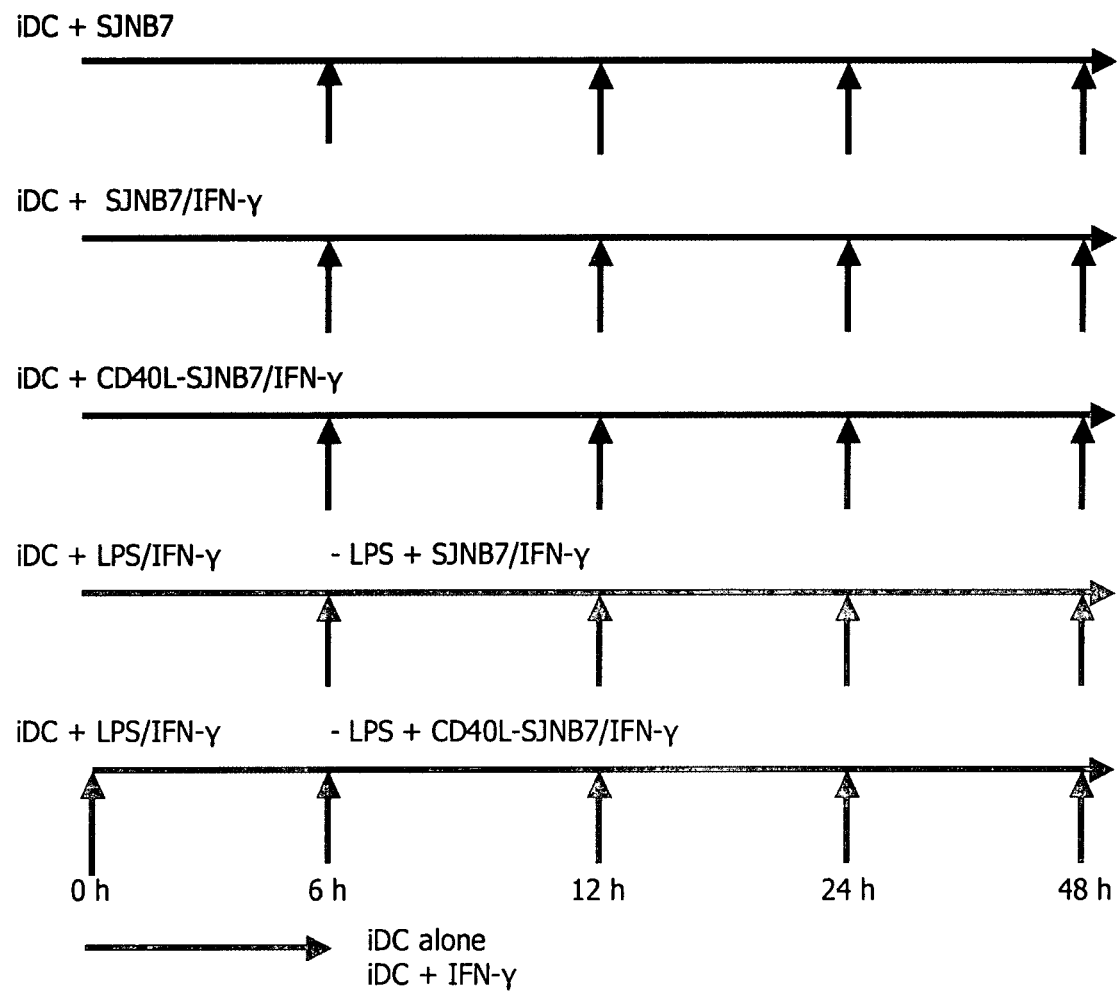
FIG. 8 shows the experimental design of the DC expression profiling experiments.

Whole genome DNA micro arrays were used to generate expression profiles of DCs exposed to the maturation stimulus LPS/IFN-γ, to CD40L/IFN-γ signalling, or to a combination of LPS/IFN-γ/CD40L signalling, as well as the appropriate controls (FIG. 8).

FIG. 8 shows DC expression profiling. DCs were exposed to the indicated maturation stimuli or were left immature. RNA was extracted at the indicated time points and subjected to expression profiling using whole genome DNA micro arrays. The results of the expression profiling was analysed using CarmaWeb (Comprehensive R based Microarray Analysis, Bioinformatics Graz and the Tyrolean Cancer Research Institute, Austria). All data were grouped into 20 clusters that used the basic algorithm of the CarmaWeb software platform and identified the clusters that contained IDO and IL-10. The genes in these clusters have an expression profile similar to that of the two known immune suppressive DC molecules, which led to the conclusion that they have a function in the immune regulation of a DC that is also immune suppressive (tables 3 and 4).

TABLE 3

IDO expression cluster.

| Unique ID | Name | 6 hours LPS IFN-γ vs. 6 hours iDC M | 12 hours LPS CD40L IFN-γ vs. 12 hours iDC M | 24 hours LPS CD40L IFN-γ vs. 24 hours iDC M | 48 hours LPS CD40L IFN-γ vs. 48 hours iDC M |
|---|---|---|---|---|---|
| 210118_s_at | IL1A | 12.5712385 | 12.656363 | 11.625489 | 9.828246 |
| 1405_i_at | CCL5 | 9.775104 | 10.949544 | 12.230392 | 11.143438 |
| 1552995_at | IL27 | 10.449822 | 10.585213 | 10.862312 | 8.519849 |
| 1554997_a_at | PTGS2 | 11.7640085 | 9.820589 | 11.614364 | 11.624819 |
| 1555759_a_at | CCL5 | 12.916491 | 12.965171 | 12.63708 | 12.723415 |
| 1556378_a_at | LOC401530 | 5.897853 | 10.2600975 | 12.640888 | 13.004906 |
| 1570388_a_at | LOC401530 | 3.8191023 | 9.072843 | 11.445329 | 11.711242 |
| 202269_x_at | GBP1 | 8.517265 | 8.2832775 | 8.787927 | 8.968534 |
| 202411_at | IFI27 | 9.403024 | 9.560578 | 9.054876 | 8.233445 |
| 203828_s_at | IL32 | 9.310799 | 8.968001 | 10.09564 | 9.038413 |
| 203915_at | CXCL9 | 13.417887 | 13.097824 | 12.633152 | 11.7289915 |
| 204439_at | IFI44L | 11.743961 | 9.8876705 | 7.0858197 | 6.4474745 |
| 204470_at | CXCL1 | 10.931133 | 8.087279 | 8.933327 | 5.9426484 |
| 204533_at | CXCL10 | 9.392692 | 10.44239 | 10.786983 | 11.601183 |
| 204655_at | CCL5 | 9.542912 | 11.558153 | 11.215681 | 11.169104 |
| 204698_at | ISG20 | 12.59375 | 10.52378 | 9.431844 | 8.965937 |
| 204748_at | PTGS2 | 12.489249 | 7.144587 | 7.9113717 | 8.436964 |
| 205013_s_at | ADORA2A | 10.245063 | 8.496423 | 10.054197 | 9.867236 |
| 205067_at | IL1B | 12.89035 | 7.7892747 | 11.259029 | 11.700619 |
| 205207_at | IL6 | 7.463433 | 7.6129217 | 8.461436 | 8.870339 |
| 205476_at | CCL20 | 12.470199 | 12.587071 | 13.649405 | 12.875935 |
| 205569_at | LAMP3 | 6.9127846 | 9.671546 | 9.207934 | 10.519818 |
| 205599_at | TRAF1 | 8.448494 | 9.332896 | 9.679705 | 11.050019 |
| 205680_at | MMP10 | 6.9289026 | 9.5307 | 11.131636 | 11.908984 |
| 205681_at | BCL2A1 | 12.63274 | 12.276044 | 12.321126 | 12.00514 |
| 205692_s_at | CD38 | 11.776373 | 10.918448 | 8.890723 | 6.572375 |
| 205890_s_at | UBD | 11.738066 | 11.718061 | 12.080868 | 11.735866 |
| 206025_s_at | TNFAIP6 | 12.46147 | 9.442592 | 10.791083 | 10.010692 |
| 206026_s_at | TNFAIP6 | 8.55364 | 8.492605 | 8.934455 | 8.366126 |
| 206337_at | CCR7 | 8.625213 | 10.63397 | 11.733897 | 11.844164 |
| 206341_at | IL2RA | 7.962748 | 9.035077 | 10.360973 | 8.479506 |
| 206765_at | KCNJ2 | 4.7675686 | 9.681816 | 10.2331705 | 9.70106 |
| 206881_s_at | LILRA3 | 9.8311825 | 9.066225 | 9.314402 | 5.396609 |
| 207113_s_at | TNF | 12.704884 | 13.268166 | 11.278352 | 8.395802 |
| 207160_at | IL12A | 9.43968 | 13.149242 | 13.380418 | 8.626079 |
| 207176_s_at | CD80 | 8.31917 | 7.76368 | 8.680011 | 8.573913 |
| 207375_s_at | IL15RA | 9.771918 | 10.090428 | 10.584916 | 10.606205 |
| 207536_s_at | TNFRSF9 | 6.231527 | 7.7779512 | 9.701627 | 9.752483 |
| 207901_at | IL12B | 12.714132 | 13.101075 | 13.353125 | 7.458026 |
| 209813_x_at | TRGV9 | 3.9887655 | 10.498012 | 10.522085 | 8.133455 |

TABLE 3-continued

IDO expression cluster.

| Unique ID | Name | 6 hours LPS IFN-γ vs. 6 hours iDC M | 12 hours LPS CD40L IFN-γ vs. 12 hours iDC M | 24 hours LPS CD40L IFN-γ vs. 24 hours iDC M | 48 hours LPS CD40L IFN-γ vs. 48 hours iDC M |
|---|---|---|---|---|---|
| 210029_at | INDO | 12.789924 | 10.134047 | 12.052269 | 12.43933 |
| 210072_at | CCL19 | 7.2848625 | 10.570788 | 12.461668 | 11.943225 |
| 210163_at | CXCL11 | 13.109848 | 12.912714 | 11.681597 | 10.053444 |
| 210511_s_at | INHBA | 12.3267975 | 12.957313 | 10.577578 | 10.25125 |
| 211122_s_at | CXCL11 | 13.135339 | 13.034375 | 12.199861 | 9.8954315 |
| 211269_s_at | IL2RA | 7.485799 | 9.023119 | 10.643187 | 10.435802 |
| 213497_at | ABTB2 | 6.1966333 | 8.42709 | 9.347927 | 9.879564 |
| 215806_x_at | TRGC2 | 4.249278 | 10.289696 | 10.347067 | 7.9237046 |
| 217546_at | MT1M | 6.80711 | 8.103879 | 9.402974 | 8.6524935 |
| 219159_s_at | SLAMF7 | 12.195147 | 10.547217 | 8.994919 | 6.4161515 |
| 219424_at | EBI3 | 10.374818 | 11.288197 | 12.070472 | 10.607756 |
| 220054_at | IL23A | 6.8979635 | 12.20336 | 13.634168 | 11.491903 |
| 222838_at | SLAMF7 | 12.751745 | 12.511322 | 10.977879 | 8.82794 |
| 226560_at | SGPP2 | 10.281151 | 9.231938 | 9.82061 | 8.582578 |
| 227140_at | INHBA | 12.689469 | 10.28581 | 10.5587015 | 10.436948 |
| 227180_at | ELOVL7 | 8.1362 | 8.21396 | 9.105779 | 9.419119 |
| 229437_at | BIC | 9.607157 | 11.00861 | 11.168569 | 11.648725 |
| 229625_at | GBP5 | 11.195785 | 11.012673 | 7.085479 | 8.598587 |
| 231577_s_at | GBP1 | 7.464914 | 8.356869 | 8.556055 | 8.40867 |
| 235229_at |  | 8.6328745 | 8.228744 | 8.894646 | 8.620824 |
| 238439_at | ANKRD22 | 7.496807 | 7.9435267 | 8.688104 | 10.303624 |
| 238581_at | GBP5 | 9.960986 | 9.9203 | 7.430702 | 7.571562 |
| 238725_at |  | 5.625349 | 7.5093164 | 9.704128 | 10.179434 |
| 240287_at | LOC341720 | 10.947632 | 11.357612 | 9.703499 | 4.2557507 |
| 242814_at | SERPINB9 | 9.147152 | 9.357069 | 9.150615 | 9.138746 |
| 33304_at | ISG20 | 11.309338 | 7.729137 | 8.4003 | 6.2511134 |
| 39402_at | IL1B | 12.057478 | 6.510902 | 10.422022 | 11.546757 |
| 228439_at | MGC20410 | 6.443625 | 4.5576925 | 5.1437 | 2.8559468 |
| 232078_at | PVRL2 | 6.135475 | 4.746409 | 3.8879604 | 4.522022 |
| 1561908_a_at | HS3ST3B1 | 7.0928926 | 4.458722 | 3.670319 | 3.8414023 |
| 204141_at | TUBB2 | 5.3551335 | 4.7444496 | 4.0537806 | 5.1056914 |
| 207275_s_at | ACSL1 | 5.8632264 | 5.869882 | 4.1483216 | 4.095168 |
| 210563_x_at | CFLAR | 5.100706 | 5.0670333 | 5.419278 | 4.1996965 |
| 210564_x_at | CFLAR | 5.380331 | 4.9984617 | 5.3778234 | 4.160804 |
| 218400_at | OAS3 | 6.8762517 | 6.1737237 | 4.410526 | 2.8219512 |
| 220132_s_at | CLEC2D | 4.4514236 | 6.669927 | 5.78131 | 1.7744006 |
| 222303_at | ETS2 | 4.60927 | 5.654717 | 5.4186363 | 3.4308143 |
| 229221_at | CD44 | 7.1867433 | 5.771355 | 3.1319969 | 4.7465234 |
| 230499_at | BIRC3 | 4.71687 | 4.9918036 | 5.3390183 | 5.366412 |
| 232682_at | DSU | 4.6348085 | 5.7252564 | 5.5562453 | 3.688244 |
| 243296_at | PBEF1 | 6.237873 | 4.170852 | 4.781295 | 5.1768007 |
| 243894_at | SLC41A2 | 7.1203766 | 4.7231464 | 4.238267 | 4.4368286 |
| 1554539_a_at | RHOF | 5.002441 | 4.1752563 | 5.4232445 | 5.0010266 |
| 1563357_at | SERPINB9 | 6.368476 | 5.3010783 | 3.9647322 | 5.4146433 |
| 202509_s_at | TNFAIP2 | 5.195548 | 5.9835477 | 4.9414105 | 3.823941 |
| 203287_at | LAD1 | 4.5966916 | 6.1679506 | 5.8620677 | 3.8349202 |
| 204715_at | PANX1 | 6.0651593 | 4.6488233 | 5.01669 | 4.461601 |
| 204794_at | DUSP2 | 5.4158106 | 3.7610755 | 4.858317 | 6.9610953 |
| 207389_at | GP1BA | 6.946879 | 6.472854 | 5.3776803 | 2.2710993 |
| 209039_x_at | EHD1 | 5.992218 | 4.9087305 | 4.788946 | 5.520831 |
| 209928_s_at | MSC | 4.9872894 | 5.956739 | 4.365724 | 5.714541 |
| 215078_at | SOD2 | 6.952513 | 7.3351035 | 3.1302252 | 3.7524989 |
| 216336_x_at | MT1M | 4.864737 | 4.9637637 | 6.200034 | 5.143623 |
| 219716_at | APOL6 | 7.687471 | 5.4070616 | 4.6342998 | 3.8593137 |
| 221779_at | MICAL-L1 | 5.128767 | 5.6324835 | 6.08239 | 4.3245826 |
| 226189_at |  | 7.0649176 | 5.7119026 | 5.3064666 | 3.6578546 |
| 227014_at | LOC57168 | 7.947885 | 4.03786 | 4.678014 | 4.4947524 |
| 232304_at | PELI1 | 6.7769756 | 5.062101 | 4.4606757 | 5.45498 |
| 234985_at | LOC143458 | 5.5271115 | 4.7101053 | 5.720184 | 4.8197145 |
| 242649_x_at | C15orf21 | 6.9237723 | 5.3964243 | 4.532885 | 4.963293 |
| 1559391_s_at | B4GALT5 | 4.598228 | 7.0806437 | 5.126474 | 4.786352 |
| 200629_at | WARS | 6.951068 | 5.0352116 | 4.546803 | 4.863137 |
| 202688_at | TNFSF10 | 6.8965373 | 5.708206 | 4.570576 | 5.1128407 |
| 202748_at | GBP2 | 5.793167 | 6.4275317 | 4.901077 | 4.8227687 |
| 203685_at | BCL2 | 7.285017 | 5.9438853 | 4.1533656 | 4.8756795 |
| 204015_s_at | DUSP4 | 8.879749 | 6.673204 | 3.3034465 | 4.2480526 |
| 204926_at | INHBA | 5.6395097 | 7.8953505 | 4.531301 | 3.1433787 |
| 206157_at | PTX3 | 7.3603053 | 5.5506916 | 5.1639824 | 4.220827 |
| 209803_s_at | PHLDA2 | 5.2155585 | 4.638463 | 6.690672 | 5.015275 |
| 209939_x_at | CFLAR | 5.3425546 | 5.3650227 | 6.3261905 | 4.451903 |
| 211302_s_at | PDE4B | 9.388175 | 4.2461367 | 4.496878 | 4.7590027 |
| 215671_at | PDE4B | 6.8900924 | 4.9770446 | 4.6578245 | 5.777932 |

TABLE 3-continued

IDO expression cluster.

| Unique ID | Name | 6 hours LPS IFN-γ vs. 6 hours iDC M | 12 hours LPS CD40L IFN-γ vs. 12 hours iDC M | 24 hours LPS CD40L IFN-γ vs. 24 hours iDC M | 48 hours LPS CD40L IFN-γ vs. 48 hours iDC M |
|---|---|---|---|---|---|
| 216705_s_at | ADA | 6.1992345 | 4.8220434 | 5.4637165 | 5.23145 |
| 218943_s_at | DDX58 | 7.6221895 | 6.2795057 | 4.79867 | 4.15005 |
| 219014_at | PLAC8 | 4.8591843 | 4.901381 | 8.194876 | 3.2458937 |
| 221087_s_at | APOL3 | 6.84244 | 5.7354436 | 4.5675263 | 5.530723 |
| 221185_s_at | IQCG | 6.629468 | 3.8091857 | 6.4129505 | 5.9112988 |
| 222812_s_at | RHOF | 5.2598224 | 5.562695 | 5.265753 | 5.8453097 |
| 239876_at | NFKB1 | 6.668459 | 5.936471 | 4.785418 | 5.0308824 |
| 240013_at |  | 5.927128 | 5.32223 | 5.1699376 | 5.818874 |
| 242234_at | BIRC4BP | 5.92746 | 5.946681 | 4.6361747 | 6.306454 |
| 35150_at | CD40 | 5.5139947 | 5.5919642 | 6.1309977 | 5.227399 |
| 1553713_a_at | RHEBL1 | 5.2900615 | 5.984809 | 5.9541264 | 5.9824634 |
| 1570253_a_at | RHEBL1 | 5.2768035 | 6.012619 | 5.687341 | 5.871174 |
| 202687_s_at | TNFSF10 | 7.8631916 | 5.812222 | 4.413325 | 5.5924144 |
| 204415_at | G1P3 | 4.8981137 | 6.400349 | 6.9897156 | 3.8297942 |
| 205483_s_at | G1P2 | 6.6436443 | 6.099025 | 5.6568613 | 4.5633087 |
| 206975_at | LTA | 7.6997614 | 8.081627 | 5.2525034 | 2.2437675 |
| 214228_x_at | TNFRSF4 | 8.910944 | 6.6099103 | 3.4565573 | 5.0546947 |
| 215346_at | CD40 | 5.0572295 | 5.593753 | 6.163759 | 5.6992526 |
| 219211_at | USP18 | 8.285303 | 7.0497055 | 5.0085244 | 3.340998 |
| 223887_at | GPR132 | 6.7607636 | 4.543277 | 5.509192 | 7.0652533 |
| 226702_at | LOC129607 | 7.0691476 | 5.9127674 | 5.569863 | 5.045494 |
| 227816_at | LOC400572 | 5.9134483 | 6.345112 | 6.439589 | 5.0362144 |
| 231578_at | GBP1 | 7.4657335 | 6.917391 | 3.8039267 | 6.1784716 |
| 232213_at | PELI1 | 7.4485292 | 5.587166 | 5.212285 | 6.0972896 |
| 200628_s_at | WARS | 9.368469 | 5.516358 | 4.64247 | 5.419954 |
| 202800_at | SLC1A3 | 6.087409 | 6.9154663 | 7.895211 | 3.3894732 |
| 204014_at | DUSP4 | 8.585252 | 6.8769712 | 4.5652914 | 4.590569 |
| 204070_at | RARRES3 | 5.2620735 | 6.591536 | 6.2708507 | 5.70036 |
| 204747_at | IFIT3 | 8.602514 | 7.492393 | 5.6343427 | 3.3676317 |
| 212458_at | SPRED2 | 5.5534644 | 7.490529 | 6.08654 | 4.736595 |
| 212641_at | HIVEP2 | 6.433779 | 5.7410865 | 6.5065494 | 6.1581783 |
| 231779_at | IRAK2 | 8.596796 | 4.4581327 | 5.576258 | 6.910897 |
| 1559777_at |  | 5.605326 | 8.543147 | 6.0953383 | 4.9331293 |
| 200986_at | SERPING1 | 9.492846 | 8.300845 | 4.229471 | 3.6452117 |
| 203708_at | PDE4B | 11.223041 | 4.007264 | 4.071895 | 4.2633905 |
| 204286_s_at | PMAIP1 | 9.400938 | 5.3456664 | 4.7092376 | 6.7266498 |
| 205153_s_at | CD40 | 6.071054 | 6.5306187 | 6.4112535 | 6.4513636 |
| 222934_s_at | CLEC4E | 8.080958 | 8.404435 | 6.981838 | 2.577743 |
| 224225_s_at | ETV7 | 7.935058 | 6.064494 | 6.699362 | 5.50029 |
| 226474_at | NOD27 | 5.9191046 | 7.2645817 | 5.1934004 | 7.0305643 |
| 227262_at | HAPLN3 | 7.1910353 | 6.615262 | 5.1981425 | 7.5915074 |
| 230127_at |  | 7.3191285 | 7.9864871 | 5.3266 | 6.0064306 |
| 244780_at | SGPP2 | 8.127058 | 5.944443 | 6.879924 | 5.023631 |
| 1569095_at |  | 7.318123 | 8.3700075 | 6.2253203 | 4.625397 |
| 201601_x_at | IFITM1 | 7.6313257 | 7.573814 | 6.0775313 | 4.9257803 |
| 202643_s_at | TNFAIP3 | 6.250073 | 5.1900063 | 6.5136204 | 7.95266 |
| 202760_s_at | PALM2-AKAP2 | 9.142822 | 7.253937 | 5.7028017 | 5.2498336 |
| 204285_s_at | PMAIP1 | 10.275632 | 5.124492 | 4.698287 | 7.937848 |
| 204363_at | F3 | 5.9613805 | 7.1758485 | 7.078458 | 5.787101 |
| 208747_s_at | C1S | 6.224019 | 6.8833885 | 6.2983246 | 6.745276 |
| 209723_at | SERPINB9 | 10.339775 | 5.989251 | 4.825143 | 6.5091825 |
| 214329_x_at | TNFSF10 | 6.1703367 | 6.8099036 | 6.2552257 | 7.0860806 |
| 216598_s_at | CCL2 | 7.959111 | 5.9420986 | 7.541988 | 5.4770517 |
| 218656_s_at | LHFP | 5.799256 | 5.6268 | 7.0819764 | 6.887103 |
| 221680_s_at | ETV7 | 7.4525156 | 6.8642745 | 6.899157 | 6.077394 |
| 227677_at | JAK3 | 5.4577355 | 5.5538926 | 6.847657 | 6.6245513 |
| 229450_at | IFIT3 | 7.4833083 | 7.133669 | 7.3032265 | 5.366725 |
| 235574_at | GBP4 | 8.758058 | 7.3968883 | 5.5135446 | 6.7058306 |
| 1554519_at | CD80 | 7.0503464 | 5.5513606 | 6.9412417 | 7.924613 |
| 1555689_at | CD80 | 8.324632 | 7.511187 | 6.2935348 | 6.2964225 |
| 204224_s_at | GCH1 | 7.3962016 | 6.945448 | 5.8722777 | 7.290103 |
| 205114_s_at | CCL3 | 8.18418 | 6.780873 | 7.019624 | 5.952113 |
| 206508_at | TNFSF7 | 6.858301 | 7.575267 | 8.330129 | 4.665465 |
| 209722_s_at | SERPINB9 | 8.607762 | 7.3330297 | 5.989785 | 6.4565625 |
| 213524_s_at | G0S2 | 7.547209 | 7.6664352 | 6.440924 | 6.2842937 |
| 222292_at | CD40 | 8.530226 | 8.246122 | 6.060198 | 6.302727 |
| 223798_at | SLC41A2 | 9.232196 | 8.087529 | 3.90797 | 7.397384 |
| 242907_at | GBP2 | 7.746566 | 8.2072735 | 5.8188763 | 6.584134 |
| 1555465_at | MCOLN2 | 9.518959 | 8.71965 | 6.8508315 | 4.539327 |
| 200953_s_at | CCND2 | 7.411466 | 6.296918 | 7.8509226 | 6.8842726 |
| 201860_s_at | PLAT | 8.657469 | 7.604994 | 6.370206 | 6.5896416 |
| 208303_s_at | CRLF2 | 8.685696 | 8.653402 | 8.276672 | 3.62456 |

TABLE 3-continued

IDO expression cluster.

| Unique ID | Name | 6 hours LPS IFN-γ vs. 6 hours iDC M | 12 hours LPS CD40L IFN-γ vs. 12 hours iDC M | 24 hours LPS CD40L IFN-γ vs. 24 hours iDC M | 48 hours LPS CD40L IFN-γ vs. 48 hours iDC M |
|---|---|---|---|---|---|
| 238727_at | LOC440934 | 7.688413 | 7.8426127 | 7.593639 | 5.8430877 |
| 239186_at | MGC39372 | 7.809087 | 6.8687167 | 7.7233596 | 6.9605627 |
| 222221_x_at | EHD1 | 7.799284 | 6.630239 | 7.478602 | 7.7974253 |
| 222326_at | PDE4B | 8.487402 | 7.4390974 | 5.838442 | 8.485796 |
| 223767_at | GPR84 | 9.556347 | 9.886792 | 8.25461 | 2.6693628 |
| 214022_s_at | IFITM1 | 8.305978 | 9.906662 | 6.8351192 | 5.3545113 |
| 221241_s_at | BCL2L14 | 7.763052 | 8.927696 | 7.4124217 | 6.0943 |
| 209037_s_at | EHD1 | 6.202972 | 6.62678 | 6.968862 | 8.198914 |
| 222802_at |  | 9.193985 | 9.879644 | 6.7598433 | 5.578077 |
| 234306_s_at | SLAMF7 | 11.054989 | 9.386422 | 7.5571413 | 4.0329967 |
| 219584_at | PLA1A | 7.8830075 | 8.5753975 | 7.899431 | 6.5355268 |
| 232593_at | LINCR | 7.426831 | 7.1173863 | 7.508543 | 8.483282 |
| 235175_at | GBP4 | 8.098684 | 8.014575 | 6.7604356 | 8.305143 |
| 238567_at | SGPP2 | 9.60297 | 7.9624267 | 8.190959 | 5.9755754 |
| 202270_at | GBP1 | 7.857806 | 7.5784187 | 7.864753 | 7.7254214 |
| 206058_at | SLC6A12 | 7.0730734 | 7.6346216 | 7.868434 | 7.8353267 |
| 209270_at | LAMB3 | 6.3819847 | 7.637574 | 8.068874 | 8.396816 |
| 223217_s_at | NFKBIZ | 6.579339 | 5.8985357 | 7.933263 | 9.0830765 |
| 230110_at | MCOLN2 | 7.0183334 | 8.743037 | 8.322358 | 6.695663 |
| 235116_at | TRAF1 | 7.515788 | 6.6126266 | 7.946375 | 8.608736 |
| 239196_at | ANKRD22 | 6.893366 | 7.2058015 | 7.997893 | 8.679558 |
| 1557359_at | LOC285758 | 5.7492123 | 6.7752757 | 6.428899 | 8.264215 |
| 202833_s_at | SERPINA1 | 6.047883 | 6.2670393 | 8.372422 | 8.15069 |
| 220655_at | TNIP3 | 4.227455 | 9.260285 | 8.14861 | 3.8333952 |
| 210354_at | IFNG | 7.0490704 | 9.9158745 | 9.995628 | 4.7299943 |
| 239331_at |  | 4.9562793 | 7.907742 | 6.738407 | 7.5105863 |

According to the CarmaWeb algorithm, the genes listed have an expression profile that resembles that of IDO (gene name INDO) suggesting a function similar to that of IDO (numbers are log with base 2 relative to immature DCs).

TABLE 4

IL-10 expression cluster.

| Unique ID | Name | 6 hours LPS IFN-γ vs. 6 hours iDC M | 12 hours LPS CD40L IFN-γ vs. 12 hours iDC M | 24 hours LPS CD40L IFN-γ vs. 24 hours iDC M | 48 hours LPS CD40L IFN-γ vs. 48 hours iDC M |
|---|---|---|---|---|---|
| 1556300_s_at |  | 0 | 4.323714 | 1.5688843 | 0.257391 |
| 1556378_a_at | LOC401530 | 0 | 3.3170495 | −0.124789566 | 1.3912028 |
| 1556883_a_at | LOC401528 | 0 | 4.490707 | −0.14703345 | 2.7003522 |
| 202291_s_at | MGP | 0 | 5.571205 | 2.098167 | 0.038769286 |
| 202878_s_at | C1QR1 | 0 | 3.306639 | 0.3353752 | 1.2330873 |
| 204475_at | MMP1 | 0 | 5.03655 | 0.2590128 | 0.17097393 |
| 204614_at | SERPINB2 | 0 | 3.4892087 | 2.2649622 | 0.08403955 |
| 205676_at | CYP27B1 | 0 | 3.6301327 | 0.1309929 | 0.7396309 |
| 223287_at | FOXP1 | 0 | 2.983712 | 1.7371364 | 0.5753527 |
| 224773_at | NAV1 | 0 | 3.3603613 | 0.35192382 | 0.9197203 |
| 227812_at | TNFRSF19 | 0 | 3.3981404 | 1.6189107 | 0.044692483 |
| 235042_at | CMYA1 | 0 | 3.450752 | 0.328667 | 1.5720363 |
| 235444_at | FOXP1 | 0 | 3.0461197 | −0.042442646 | 1.3964777 |
| 241860_at | STK17B | 0 | 2.671234 | 0.61670065 | 1.4493694 |
| 1556582_at | LOC440536 | 0 | 2.6907892 | 1.2484756 | 1.1807224 |
| 1564028_s_at | FLJ40722 | 0 | 2.750025 | 0.67192906 | 1.4337206 |
| 1566480_x_at | FLJ31795 | 0 | 2.810023 | 1.4379538 | 0.6065171 |
| 1570388_a_at | LOC401530 | 0 | 3.911918 | 0.027789168 | 1.8137968 |
| 202877_s_at | C1QR1 | 0 | 3.3630056 | 0.6407456 | 1.4440103 |
| 204602_at | DKK1 | 0 | 3.921798 | 3.6861098 | 0.3208148 |
| 204932_at | TNFRSF11B | 0 | 4.2726865 | 3.2933848 | 0.21878207 |
| 215268_at | MACF1 | 0 | 2.6788146 | 1.2724367 | 0.8143623 |
| 216497_at | LOC120364 | 0 | 2.3947499 | 1.1637448 | 0.9242658 |
| 216867_s_at | PDGFA | 0 | 2.1128201 | 1.2416315 | 1.132686 |
| 220655_at | TNIP3 | 0 | 3.474797 | 0.8904967 | 1.8436728 |
| 221870_at | EHD2 | 0 | 2.571253 | 0.94932306 | 1.2732899 |
| 224771_at | NAV1 | 0 | 3.8266947 | 1.5089604 | 1.4963266 |
| 238712_at |  | 0 | 4.2949014 | 1.8307322 | 2.142599 |
| 239311_at | DHX57 | 0 | 2.27365 | 1.3914022 | 1.0178465 |
| 1556318_s_at | CAND1 | 0 | 2.3933206 | 0.9396068 | 1.3715496 |

TABLE 4-continued

IL-10 expression cluster.

| Unique ID | Name | 6 hours LPS IFN-γ vs. 6 hours iDC M | 12 hours LPS CD40L IFN-γ vs. 12 hours iDC M | 24 hours LPS CD40L IFN-γ vs. 24 hours iDC M | 48 hours LPS CD40L IFN-γ vs. 48 hours iDC M |
|---|---|---|---|---|---|
| 227732_at | ATXN7L1 | 0 | 3.4273734 | 0.6846624 | 2.2728565 |
| 239060_at | EHD1 | 0 | 1.997289 | 0.32936123 | 1.8916218 |
| 206176_at | BMP6 | 0 | 2.2903044 | −0.18439728 | 2.1745071 |
| 207386_at | CYP7B1 | 0 | 3.9868062 | 0.7309004 | 2.746021 |
| 210229_s_at | CSF2 | 0 | 3.1023788 | −0.1405712 | 2.5077276 |
| 215750_at | KIAA1659 | 0 | 3.0428922 | −0.006880157 | 2.480364 |
| 225025_at | IGSF8 | 0 | 1.905534 | 0.49440768 | 1.845558 |
| 227345_at | TNFRSF10D | 0 | 2.1187048 | 0.36650723 | 2.0576801 |
| 236738_at | LOC401097 | 0 | 2.4518428 | 1.685922 | 1.7134967 |
| 242517_at | GPR54 | 0 | 1.9395804 | 0.21328141 | 2.186202 |
| 228910_at | CD82 | 0 | 3.5779603 | 1.2853656 | 2.5263379 |
| 229307_at | ANKRD28 | 0 | 3.1102884 | 0.8216141 | 2.5533133 |
| 231832_at | GALNT4 | 0 | 2.2378833 | 0.72167736 | 2.091024 |
| 37005_at | NBL1 | 0 | 2.158463 | 1.2050192 | 2.0193584 |
| 227410_at | FAM43A | 0 | 3.1527455 | 1.5260311 | 2.2625198 |
| 228625_at | CITED4 | 0 | 2.2035446 | 0.8985138 | 2.1428196 |
| 240432_x_at | | 0 | 2.0101619 | 1.3507649 | 2.0001297 |
| 203074_at | ANXA8 | 0 | 2.754555 | 0.79692614 | 2.6273892 |
| 206009_at | ITGA9 | 0 | 1.9594706 | 0.54135984 | 2.3522627 |
| 235438_at | | 0 | 4.0041165 | 0.70460325 | 3.542835 |
| 1560869_a_at | | 0 | 2.5460286 | 1.5980372 | 2.5416172 |
| 223525_at | DLL4 | 0 | 3.5447857 | 0.5724994 | 3.72409 |
| 232090_at | DNM3 | 0 | 4.302288 | 3.442975 | 2.8309567 |
| 203904_x_at | CD82 | 0 | 2.0282779 | 1.3777583 | 2.4270318 |
| 225645_at | EHF | 0 | 4.428559 | 2.14202 | 3.7522347 |
| 235737_at | TSLP | 0 | 4.959613 | 1.5306113 | 4.4908447 |
| 202237_at | NNMT | 0 | 3.6071026 | 3.2686546 | 2.8587787 |
| 207433_at | IL10 | 0 | 4.00954 | 1.7226876 | 3.7454016 |
| 214414_x_at | HBA1 | 0 | 2.1132698 | 1.575519 | 2.6071193 |
| 224940_s_at | PAPPA | 0 | 2.786031 | 2.7599206 | 0.7074637 |
| 212730_at | DMN | 0 | 3.6943512 | 0.91267496 | 4.2896175 |
| 219874_at | SLC12A8 | 0 | 2.8926702 | 3.182794 | 1.9976637 |
| 224646_x_at | H19 | 0 | 2.466048 | 2.7163086 | 2.6425989 |
| 209324_s_at | RGS16 | 0 | 3.3799229 | 2.467596 | 3.7553544 |
| 243788_at | PHF11 | 0 | 2.1383092 | 2.2994013 | 2.1082926 |
| 202238_s_at | NNMT | 0 | 4.160124 | 4.563192 | 3.5705357 |
| 224997_x_at | H19 | 0 | 2.8080769 | 3.1897178 | 3.0020173 |
| 236176_at | | 0 | 2.051894 | 0.7956073 | 3.2491539 |
| 44790_s_at | C13orf18 | 0 | 2.1295624 | 2.4644802 | 2.7274456 |
| 206825_at | OXTR | 0 | 2.7509916 | 0.5947344 | 4.1146626 |
| 207442_at | CSF3 | 0 | 2.2279809 | 1.6218964 | 3.2061028 |
| 216575_at | | 0 | 2.1809235 | 1.0562297 | 3.4115193 |
| 237559_at | GPR55 | 0 | 2.0120387 | 1.6486369 | 3.2241027 |
| 200951_s_at | CCND2 | 0 | −0.061742224 | 2.055891 | 5.531777 |
| 204163_at | EMILIN1 | 0 | −0.08650574 | 2.116541 | 3.2442234 |
| 215546_s_at | CSPG2 | 0 | 1.0869541 | 0.9552003 | 4.6304297 |
| 220442_at | GALNT4 | 0 | 1.6785349 | 2.2396698 | 2.8896742 |
| 223194_s_at | C6orf85 | 0 | 1.4545181 | 1.8726805 | 3.2625294 |
| 227703_s_at | SYTL4 | 0 | −0.012060306 | 2.8051267 | 3.7273147 |
| 1552393_at | FLJ25421 | 0 | −0.008524944 | 0.79469424 | 4.0263605 |
| 1552394_a_at | FLJ25421 | 0 | 0.4518348 | 1.1220381 | 3.568555 |
| 1553785_at | RASGEF1B | 0 | 0.8244259 | 3.0841393 | 2.744691 |
| 1554079_at | GALNTL4 | 0 | 0.80384594 | 2.1117246 | 3.2543478 |
| 1559777_at | | 0 | 1.373273 | 1.964059 | 4.745006 |
| 1562433_at | FLJ10489 | 0 | 0.26058874 | 3.4475367 | 4.6152167 |
| 1568949_at | PITPNC1 | 0 | 0.004084121 | 2.9905202 | 3.3454092 |
| 1569095_at | | 0 | 1.0567621 | 1.0456768 | 3.5029418 |
| 200783_s_at | STMN1 | 0 | 0.2741603 | 1.4904935 | 3.2696452 |
| 202403_s_at | COL1A2 | 0 | 0.83871436 | 2.151641 | 3.4803479 |
| 202431_s_at | MYC | 0 | 1.0226223 | 2.5720317 | 3.490832 |
| 202998_s_at | LOXL2 | 0 | 0.4333325 | 1.7000065 | 3.451721 |
| 203108_at | GPRC5A | 0 | 1.6255034 | 1.8504707 | 4.352528 |
| 203131_at | PDGFRA | 0 | −0.45237933 | 1.4600621 | 3.411754 |
| 203592_s_at | FSTL3 | 0 | 0.14812845 | 2.2247574 | 3.3438997 |
| 203980_at | FABP4 | 0 | −0.009128572 | 1.3565757 | 4.341141 |
| 204301_at | KIAA0711 | 0 | −0.015199099 | 1.469634 | 3.7521276 |
| 204411_at | KIF21B | 0 | 0.99417245 | 2.3202088 | 3.2713737 |
| 204619_s_at | CSPG2 | 0 | 1.7562126 | 1.4990444 | 4.1206384 |
| 204620_s_at | CSPG2 | 0 | 1.6183093 | 1.011578 | 4.371935 |
| 204879_at | PDPN | 0 | −0.15425473 | 0.95934194 | 3.9027925 |
| 204904_at | GJA4 | 0 | 0.30981743 | 2.2777586 | 3.7517166 |
| 205100_at | GFPT2 | 0 | 1.5140616 | 1.8844032 | 5.630774 |

TABLE 4-continued

IL-10 expression cluster.

| Unique ID | Name | 6 hours LPS IFN-γ vs. 6 hours iDC M | 12 hours LPS CD40L IFN-γ vs. 12 hours iDC M | 24 hours LPS CD40L IFN-γ vs. 24 hours iDC M | 48 hours LPS CD40L IFN-γ vs. 48 hours iDC M |
|---|---|---|---|---|---|
| 205289_at | BMP2 | 0 | 0.60859656 | 1.5663037 | 3.305952 |
| 205290_s_at | BMP2 | 0 | 0.07147631 | 1.7073456 | 4.3988748 |
| 205826_at | MYOM2 | 0 | −0.004983342 | 3.2177415 | 6.163263 |
| 205861_at | SPIB | 0 | 0.7059429 | 2.4294124 | 2.704671 |
| 205898_at | CX3CR1 | 0 | −0.010416569 | 2.8846204 | 5.349967 |
| 206027_at | S100A3 | 0 | 0.13657278 | 1.5692319 | 3.4727564 |
| 206090_s_at | DISC1 | 0 | −0.8741116 | 1.8682606 | 5.05058 |
| 206729_at | TNFRSF8 | 0 | 0.27889317 | 2.6180744 | 5.8870077 |
| 206741_at | LOC51066 | 0 | 0.47887027 | 2.5547576 | 5.7319098 |
| 206859_s_at | PAEP | 0 | −0.001321607 | 1.3401538 | 3.7394311 |
| 207510_at | BDKRB1 | 0 | 2.0661907 | 3.4934416 | 3.781754 |
| 209325_s_at | RGS16 | 0 | 1.5113075 | 2.5088499 | 3.8291175 |
| 210095_s_at | IGFBP3 | 0 | 0.21584912 | 2.5991304 | 3.2872534 |
| 211372_s_at | IL1R2 | 0 | −0.6165594 | 1.6310264 | 3.7544057 |
| 211571_s_at | CSPG2 | 0 | 0.91350543 | 0.87646186 | 5.6404405 |
| 211596_s_at | LRIG1 | 0 | 3.8467457 | 2.826491 | 5.69805 |
| 211597_s_at | HOP | 0 | 0.1277425 | 1.6993432 | 6.786917 |
| 212143_s_at | IGFBP3 | 0 | −0.19099335 | 3.7475343 | 4.0994177 |
| 212444_at | | 0 | 1.1151347 | 1.3201189 | 3.6738355 |
| 213139_at | SNAI2 | 0 | 0.001255514 | 3.9536047 | 5.2359695 |
| 215495_s_at | SAMD4 | 0 | −0.6807276 | 2.1140902 | 4.5931683 |
| 218574_s_at | LMCD1 | 0 | 0.004399216 | 0.005991654 | 4.832267 |
| 218975_at | COL5A3 | 0 | 1.8476033 | 3.2505863 | 4.3477015 |
| 219168_s_at | PRR5 | 0 | 0.3802334 | 1.883373 | 5.4903607 |
| 219181_at | LIPG | 0 | 0.034028087 | 1.7650458 | 4.60227 |
| 221731_x_at | CSPG2 | 0 | 1.1740024 | 1.1199198 | 4.3726726 |
| 224950_at | PTGFRN | 0 | 0.2711382 | 2.548231 | 4.0687737 |
| 225571_at | LIFR | 0 | 1.2333707 | 2.1292431 | 2.7829444 |
| 226621_at | FGG | 0 | 0.91611135 | 2.2092934 | 3.1336222 |
| 227256_at | USP31 | 0 | 0.66912067 | 1.812497 | 3.3547237 |
| 228245_s_at | OVOS2 | 0 | −0.6036949 | 1.9032807 | 5.509818 |
| 228367_at | ALPK2 | 0 | 1.9285325 | 1.4045739 | 3.7516391 |
| 228854_at | | 0 | 0.013371324 | 1.4183841 | 4.6363435 |
| 229247_at | FLJ37440 | 0 | 9.65E−04 | 0.14736369 | 5.156355 |
| 229622_at | FLJ43374 | 0 | 0.15105823 | 2.228979 | 3.3192601 |
| 230233_at | RASGEF1B | 0 | 0.44206667 | 2.0026255 | 4.1667137 |
| 231496_at | FCAMR | 0 | 0.0146722 | 3.7155752 | 2.9080575 |
| 231867_at | ODZ2 | 0 | −0.002545893 | −9.53E−04 | 4.766165 |
| 232739_at | SPIB | 0 | −0.03394005 | 2.8278906 | 2.699333 |
| 235100_at | | 0 | 1.1068798 | 2.099443 | 3.164012 |
| 237344_at | | 0 | 0.14466353 | 0.72832346 | 5.1735163 |
| 239808_at | PITPNC1 | 0 | −0.035855636 | 0.69854295 | 4.18631 |
| 240770_at | PRP2 | 0 | 0.35803238 | 1.2584826 | 3.8403585 |
| 242691_at | | 0 | 0.042725943 | 2.1449049 | 3.0019956 |
| 40687_at | GJA4 | 0 | −0.001706956 | 2.8572736 | 4.300132 |
| 41469_at | PI3 | 0 | 0.08784416 | 3.8997574 | 2.944381 |
| 47069_at | PRR5 | 0 | −0.30954257 | 1.9246503 | 5.094549 |
| 52255_s_at | COL5A3 | 0 | 2.9138856 | 3.5991492 | 5.075999 |
| 223503_at | DKFZP566N034 | 0 | 0.001206623 | 0.010989565 | 4.3298063 |

According to the CarmaWeb algorithm, the genes listed have an expression profile that resembles that of IL-10 (gene name IL10) suggesting a function similar to that of IL-10 (numbers are log with base 2 relative to immature DCs).

In the present DNA micro arrays, also genes were identified induced in DCs upon LPS/IFN-γ or CD40L/IFN-γ signalling with involvement in the regulation of the genes IL-10, TSLP, INDO, IL2RA, CSF-2 and CSF-3, all of which are known to have an immune suppressive effect. In order to identify potential master switches of immune regulation, a network of regulators for those genes was generated with the Pathway Studio software using Resnet 5 (version 1.2 January, 2007), a database of mammalian pathways and molecular interactions derived from PubMed and 44 open access journals. By uploading the micro array data from the differentially activated DCs to the regulatory network, potential master regulators induced in maturing DCs (table 5) could then be selected.

TABLE 5

Master switches of immune regulation.

| | Immune regulation | Affymetrix Index |
|---|---|---|
| STAT6 | IL10 | 201332_s_at |
| LITAF | IL10 | 200706_s_at |
| STAT1 | IL10, INDO, IL2RA, CSF3 | 232375_at |
| IRF4 | IL10, CSF2 | 204562_at |
| IRF1 | IL10, INDO, IL2RA | 202531_at |
| IRF2 | Not known | 203275_at |
| REL | IL10 | 206035_at |
| NFKB1 | IL10, IL2RA | 239876_at |
| STAT3 | IL2RA | 235680_at |
| RELA | IL10, IL2RA | 209878_s_at |

TABLE 5-continued

Master switches of immune regulation.

|  | Immune regulation | Affymetrix Index |
|---|---|---|
| JUNB | IL10, CSF2 | 201473_at |
| CEBPB | IL10, CSF3 | 212501_at |
| TBX21 | IL10, IL2RA | 220684_at |
| JUN | CSF2 | 201465_s_at |
| STAT5B | IL2RA | 205026_at |
| STAT5A | IL2RA, CSF2 | 203010_at |
| STAT4 | Not known | 206118_at |
| ETV6 | CSF2 | 205585_at |
| EGR1 | IL2RA | 227404_s_at |
| NFATC1 | IL10 | 210162_s_at |
| CREB1 | CSF2 | 214513_s_at |
| JAK1 | TSLP, CSF3 | 1552611_a_at |
| JAK3 | IL10, TSLP, CSF2 | 227677_at |
| LYN | IL10 | 202626_s_at |
| MAPKAPK2 | IL10 | 201460_at |
| MAP2K1 | IL10, IL2RA, CSF2 | 202670_at |
| CD274 | Not known | 223834_at |
| PDL2 | IL10 | 224399_at |
| PTGR4 | IL10, IL2RA | 204896_s_at |
| ITGAX | IL10 | 210184_at |
| ADORA2A | IL10 | 205013_s_at |
| SerpinA1 | IL10 | 202833_s_at |
| SerpinE1 | CSF2 | 202627_s_at |
| AREG | CSF2 | 205239_at |
| OSM | CSF3, CSF2 | 230170_at |
| SOCS3 | Not known | 206359_at |
| IFNG | INDO, IL2RA | 210354_at |

FIG. 9 shows examples for improved proliferative responses after knocking down the expression of target molecules in DCs identified in expression profiling using RNA interference. It is shown that the genes exhibiting a DC expression kinetic similar to IL-10, IDO, or belonging to the cluster of master switches of immune regulation are involved in negative regulatory immune suppressive feedback loops. Experiments similar to those in which the expression of IL-10 or IDO using RNA interference was knocked down were designed. DCs were transfected with siRNA specific genes from table 3, 4, or 5. Shown in FIG. 9 are the genes MAP-KAPK2, IRF2, PHF11, IRF4, JAK1, CEBPB, and ETV6. After initiation of maturation by a 6 hours exposure with LPS/IFN-g, the genetically engineered DCs were co-cultivated with allogeneic T-lymphocytes for 6 days. The allogeneic T-lymphocytes were labelled with CFSE, a fluorescent dye that enters cells, binds to proteins, and is retained inside the cell; excess CFSE was washed off. With each cell division the fluorescence intensity of the T-lymphocytes was halved, which allowed the assessment of T-lymphocyte proliferation on day 6 of the co-culture. As controls un-transfected DCs or DCs transfected with control siRNA were used. The improvement of the capacity of genetically engineered DCs to stimulate allogeneic T-lymphocytes provides evidence for the involvement of the siRNA-targeted genes in negative regulatory feedback loops. This furthermore indicates that a DC immune medicine that is genetically engineered for the knock down of such genes will have an improved therapeutic effect compared to conventional immune therapeutics.

Conclusion

Evidence is provided by the present invention that the features of a DC immune medicine may be modulated by genetic engineering. It was demonstrated that over-expression of immune stimulatory molecules in DCs as well as knock down of immune suppressive molecules results in enhanced immune stimulatory capacity. This may find an application as a DC cancer vaccine or an anti-infectious DC immune medicine, in which the DCs are charged with tumour derived antigens or antigens derived from microbes, exposed to a maturation stimulus, and engineered as described. Additionally, the data presented here imply that an immune suppressive DC medicine may be designed by knocking down immune stimulatory molecules and by over-expression of immune suppressive molecules. Such a suppressive DC immune medicine may have applications in allergy or autoimmunity, but also in transplantation medicine, in order to tolerise the transplant recipient's immune system to the transplanted tissue.

The invention claimed is:

1. A method for producing dendritic cells comprising the steps of:
    a) providing partially matured dendritic cells;
    b) contacting said partially matured dendritic cells with at least one dendritic cell maturation agent to produce partially matured dendritic cells with a capacity to secrete IL-12; and
    c) contacting the partially matured dendritic cells with a capacity to secrete IL-12 with an siRNA molecule that interferes with the expression of MAPKAPK2 in the cells to produce dendritic cells.

2. The method of claim 1, wherein the partially matured dendritic cells are obtained from skin, spleen, bone marrow, thymus, lymph nodes, umbilical cord blood, or peripheral blood.

3. The method of claim 1, wherein the at least one dendritic cell maturation agent is a lipopolysaccharide (LPS) derived from E. coli or an inactivated Gram positive or Gram negative microorganism or interferon-gamma.

4. The method of claim 3, wherein the at least one dendritic cell maturation agent is a wall constituent of BCG, an imidazoquinoline-4-amine compound or derivative thereof, a polyI:C, tumor necrosis factor α (TNFα), IL-1, IL-6, prostaglandin E6, a recombinant CD40L, a fusion protein comprising a CD40L domain, or a T-lymphocyte.

5. The method of claim 1, wherein the partially matured dendritic cells are loaded with at least one antigen.

6. The method of claim 5, wherein the at least one antigen is a
    tumor antigen, viral antigen, bacterial antigen, or any other human microbial or parasitic pathogen; or
    environmental antigen that causes allergy, auto-antigen against which an immune response can be initiated that causes disease, or transplantation antigen.

* * * * *